United States Patent [19]
Colvard

[11] Patent Number: 5,676,669
[45] Date of Patent: Oct. 14, 1997

[54] INTRAOCULAR CAPSULAR SHIELD

[76] Inventor: Michael Colvard, 14624 Sherman Way, Suite 508, Van Nuys, Calif. 91405

[21] Appl. No.: 56,115

[22] Filed: Apr. 30, 1993

[51] Int. Cl.⁶ .................................................. A61F 9/00
[52] U.S. Cl. .................................................. 606/107; 623/6
[58] Field of Search .................. 606/1, 107; 623/4, 623/6; 128/898

[56] References Cited

U.S. PATENT DOCUMENTS

| | | | |
|---|---|---|---|
| 4,251,887 | 2/1981 | Anis | 623/6 |
| 4,773,415 | 9/1988 | Tan | 606/107 |
| 4,888,016 | 12/1989 | Langerman | 606/107 |
| 5,403,323 | 4/1995 | Smith | 606/107 |

*Primary Examiner*—Glenn Dawson
*Attorney, Agent, or Firm*—Charles H. Schwartz; Ellsworth R. Roston; Milton M. Field

[57] ABSTRACT

An apparatus and method including a capsular shield for use in cataract surgery for protection of a posterior lens capsule during removal of a capsule nucleus. The shield includes a flexible, deformable soft shield having an outer configuration of a size and shape to fit within the lens capsule at a position between the nucleus and the posterior capsule to protect the posterior capsule during removal of the capsule nucleus.

33 Claims, 17 Drawing Sheets

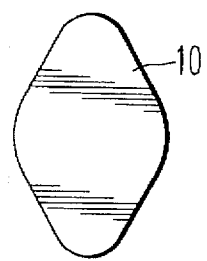
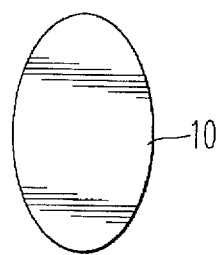
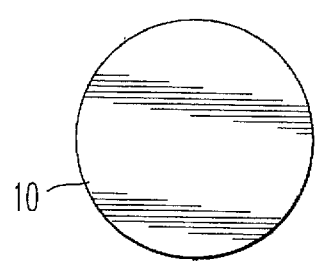
FIG. 1a          FIG. 1b          FIG. 1c
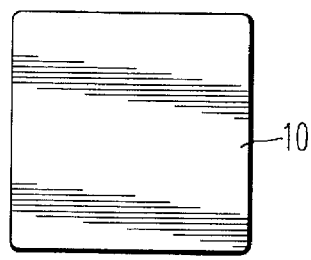
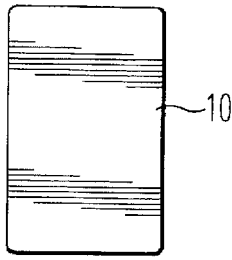
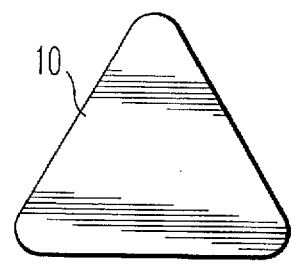
FIG. 1d          FIG. 1e          FIG. 1f
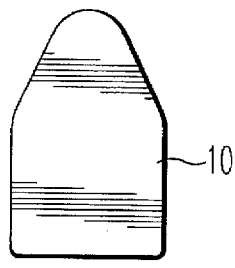
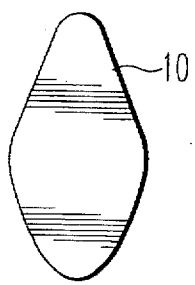
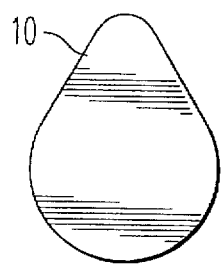
FIG. 2a          FIG. 2b          FIG. 2c
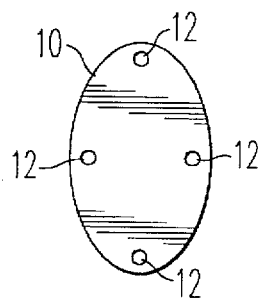
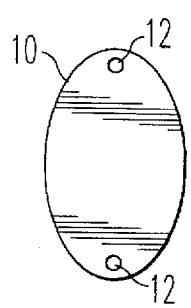
FIG. 3a          FIG. 3b

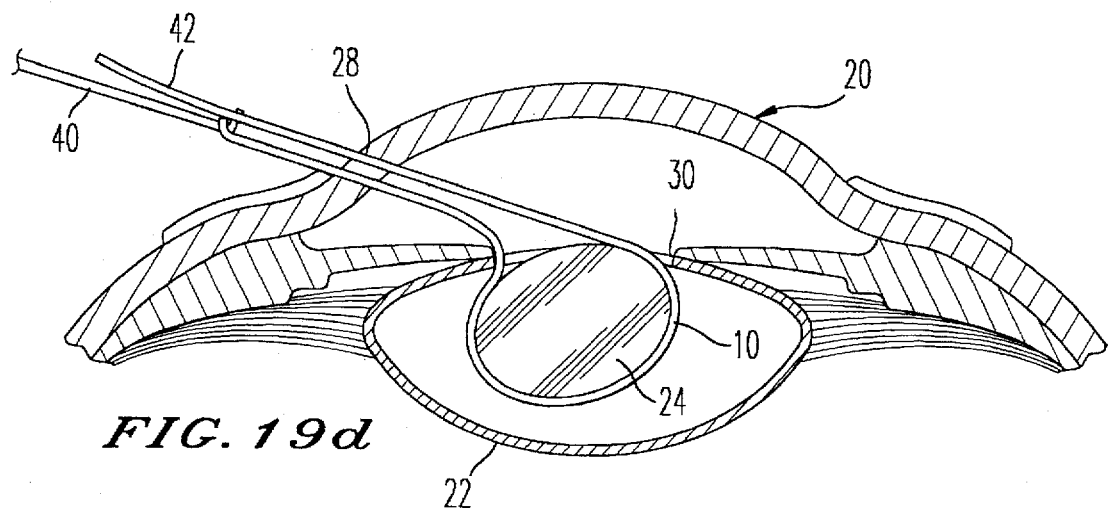
*FIG. 19d*
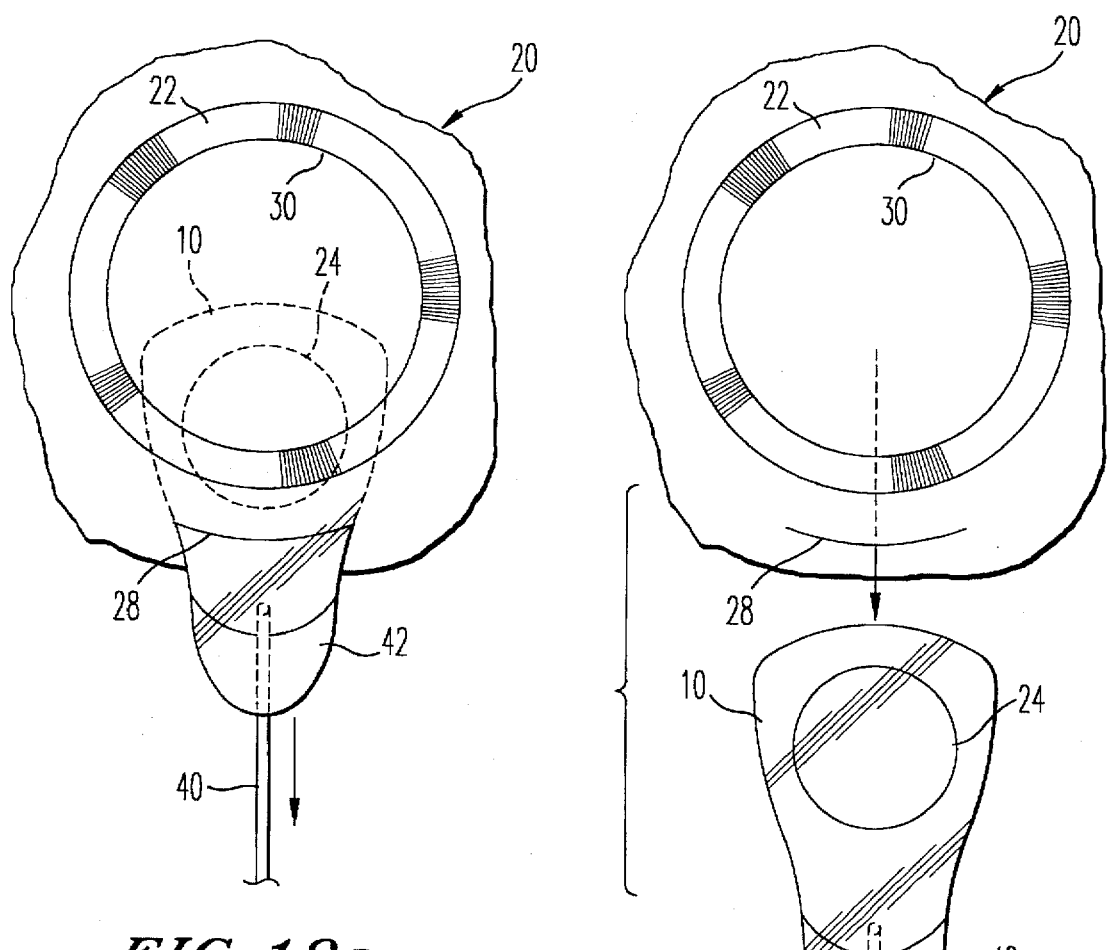
*FIG. 19e*
*FIG. 19f*

INTRAOCULAR CAPSULAR SHIELD

BACKGROUND OF THE INVENTION

The present invention relates to an intraocular capsular shield and specifically a capsular shield used during cataract surgery for protection of the posterior capsule during the extraction of the lens nucleus.

The history of cataract surgery has progressed significantly over a period of approximately forty years to the present state of the art. In the earliest days of cataract surgery and until the 1970s, the primary method for the removal of the cataract was referred to as intracapsular cataract extraction. This procedure involved the removal of the entire lens structure including the capsular bag. In particular, the extraction was accomplished by breaking the zonules to remove the lens and capsular bag as a total unit.

The above described cataract operation was effective in removing the cloudy cataract and typically vision was restored by the use of special eye glasses and later by the use of contact lenses. However, the removal of the entire lens structure including the capsular bag allowed the vitreous body, which would normally would be retained behind the capsular bag and the retina, to move forward into the anterior area of the eye. Since the vitreous body normally helps to support the retina and is not normally present in the anterior portion of the eye, the movement of the vitreous body forward can lead to a number of potential postoperative complications including relatively high incidents of retinal detachment, glaucoma, corneal decompensation, and uveitis.

Fortunately, the techniques for cataract extraction progressed beyond the early intracapsular cataract extraction and specifically, the introduction of microscopes to cataract surgery allowed surgeons to improve their techniques considerably. Specifically, cataract surgery progressed wherein the surgeon now makes an opening in the anterior capsule and removes the nucleus and cortical material while leaving the posterior capsule intact. This type of surgery is referred to as extracapsular cataract surgery and represented a significant advance in cataract surgery since it allowed the surgeon to leave the posterior capsule in place to help support the vitreous body and to keep it from moving forward in the eye. As will be appreciated, this surgical advance significantly reduced post operative complications of cataract surgery.

It should be noted that extracapsular cataract surgery had been performed before intracapsular cataract extraction, but the technology and specifically the instruments and lack of the use of a microscope made the early extracapsular surgery difficult and quite often large amounts of cortical material was left within the capsular bag. This residual cortical material often resulted in inflammation leading to serious postoperative complications.

When the early extracapsular surgery was to a large degree abandoned and surgeons turned to intracapsular cataract surgery as the primary surgical procedure, this was in a sense a step forward and backward at the same time for the reasons given above. However, with the introduction of microscopes, the cortical material could now be removed more completely and the extracapsular surgery became the preferred surgical procedure for cataracts.

As surgeons were improving their procedures for the removal of the cloudy cataract they were also making strides in the correction of vision by the introduction of intraocular lenses into the eye after the removal of the cataract. Ideally, the intraocular lens should be located at a position similar to the natural lens and with extracapsular surgery, the presence of the posterior capsule allowed the surgeon to place the intraocular lenses behind the iris within the capsule and the capsule helped to support the intraocular lens in position. This is preferable to positioning the intraocular lens in an anterior position.

one of the goals for cataract surgery is to perform the procedure using as small an incision through the eye as possible. Initially, the nucleus was removed intact which required a larger incision. In the 1970s another method for extracapsular cataract extraction was introduced, which utilized ultrasonic energy to remove the nucleus. This procedure is called phacoemulsification and allows surgeons to perform the extracapsular cataract extraction using a smaller incision than would be necessary if the nucleus was removed intact. The smaller incision is possible since the nucleus is broken up by a vibrating ultrasonic needle which forms a cannula and the nuclear material aspirated through the center of the vibrating needle.

The phacoemulsification procedure thereby allows the surgeon to remove the hard nuclear material without having to make the incision large enough to bring the entire nucleus out of the eye as a single mass. In addition to phacoemulsification, other techniques for cataract surgery which break up the nucleus into smaller pieces have been used and/or investigated. In particular, these techniques include mechanical devices which crunch the nuclear material and allow this material to be brought out of the eye in pieces.

In addition, there are devices which involve spinning and rotating cutting devices to help mechanically crush the nucleus and allow the nuclear material to be withdrawn from the eye in pieces. There have also been efforts to use an electromagnetic to cause a small propeller-like instrument to rotate within the capsule to chew up the nuclear material. Finally, laser devices are being investigated, throughout a range of wavelengths, to cut the cataract material both photoablatively and acoustically utilizing either acoustic waves or shock waves.

As indicated above, there are advantages to extracapsular cataract extraction versus intracapsular cataract extraction. However, if the posterior capsule is opened inadvertently at the time of surgery, the same types of complications can occur with extracapsular cataract extraction as would occur with intracapsular cataract extraction. Opening of the capsule results in the forward movement of the vitreous material which can result in higher incidents of retinal detachments, cystoid macular edema, glaucoma, and uveitis.

Cystoid macular edema is a swelling of a portion of the retina which effects vision. Uveitis can occur because there may be a mixing of the cataract material with the vitreous body. Both the cortical material or particles of the nucleus may cause an intense inflammatory response in the eye which can lead to the loss of vision. Therefore, loss of nuclear material into the vitreous body is one of the most serious complications of cataract surgery as the nuclear material creates an intense inflammatory reaction even more so than the cortical material.

In addition, removal of the nucleus material, if it falls into the vitreous, is very difficult and it involves an additional procedure called a "vitrectomy". In this procedure, an attempt is made to retrieve all of the material out of the vitreous body and unfortunately, efforts to do so are frequently not entirely successful. In addition, a vitrectomy, even if it removes all of the cortical material, has potential retinal complications. If not all of the cortical or nuclear material is removed from the vitreous, this may result in increased instances of cystoid macular edema, glaucoma, corneal decompensation, and uveitis. It can be seen, therefore, that it is extremely important during extracapsular cataract extraction that the posterior capsule be maintained intact and not inadvertently opened during surgery.

SUMMARY OF THE INVENTION

The present invention is thereby directed to an intraocular capsule shield and a method of using such a shield to allow extracapsular surgery to be performed while greatly decreasing the likelihood of tearing or breaking of the posterior capsule. The shield of the present invention, once it is inserted into the capsule, will prevent damage to the capsule regardless of the surgical technique employed by the surgeon. This would include all of the normal mechanical techniques used in extracapsular extraction, including crushing devices which mechanically reduce the volume of the nucleus, or ultrasonic energy as used in phacoemulsification or photic energy to photoablatively or acoustically remove the material.

The apparatus of the present invention includes a flexible, compressible, deformable or foldable soft shield which is placed between the capsule wall and the nucleus in a posterior position within the capsule. The shield may be inserted through an incision equal to or greater than the width of the shield or the shield may be rolled, deformed or compressed so that the shield may be inserted through a scleral or corneal incision which is less than the width of the shield when in the eye.

The apparatus of the present invention has the effect of reducing the likelihood of damage to the posterior capsule by protecting the capsule from mechanical, acoustic, sonic or photic damage. In addition, the apparatus of the present invention can be designed to prevent the transmission of photic energy, particularly in the UV range, to posterior structures within the eye. Specifically, the retina will be protected from such photic energy and since the retina is very sensitive to UV light, such UV light can cause severe damage to the retina.

The apparatus of the present invention has an elastic memory so that the device tends to follow the curvature of the nucleus and cradle the nuclear material. In a preferred form, the apparatus of the present invention has a C-shaped cross-sectional configuration to allow the shield to be flattened for insertion, but with the shield resuming its C-shaped configuration during and after its insertion. The insertion may be accomplished either manually or through a cylindrical insertion structure.

The C-shaped configuration helps to reduce undesired force against the capsule during the insertion and prevents injury to the capsule by the shield after insertion. This is because the C-shaped configuration provides for the leading edge of the shield curling anteriorly towards the denser nuclear material during and after insertion. Since the nuclear material is dense the nuclear material will resist the anterior curling force of the C-shaped shield and cause the shield to follow the contour of the nuclear material rather than to push against the capsule.

The shield may also be designed to have a rough posterior surface so that both during and after insertion the shield may be agitated, such as by moving the shield in a rotational direction or back and forth, to have the rough surface brush the posterior capsule and thereby clean the posterior capsule of epithelial and fibroblastic cells. Loosening and removal of these cells helps to reduce subsequent opacification of the posterior capsule. At the present time, during the surgical procedure, the surgeon uses a probe-like device with an abrasive somewhat roughened tip to scrub and polish the posterior capsule. The movement of the shield will tend to scrub away additional cortical material which is more difficult to remove with the existing procedures.

For example, with the present surgical techniques, it is very difficult for the surgeon to remove all of the cortical material and invariably a small amount of cortical material remains in the periphery of the capsule bag or a very thin layer of cortical material remains on the capsule. This material is difficult to remove using the present techniques and the movement or agitation of the shield against the capsule will facilitate the loosening and removal of this material.

The shield of the present invention may also be designed to include diopteric power to become the intraocular lens and then by eliminate a further placement of an intraocular lens. Specifically, the shield and the intraocular lens would be one and the same and in a reversal of the present surgical procedure, the shield/intraocular lens would be inserted prior to the removal of the nucleus. This method thereby constitutes a significant improvement in that the shield/intraocular lens would not only protect the capsule, but also obviate the necessity for removal of the shield/intraocular lens and make it unnecessary to place another implant lens in the eye. Using this technique, the surgical procedure would be greatly simplified.

One further advantage of the shield of the present invention is that the shield helps to maintain the capsular bag open. This facilitates the placement of the intraocular lens in the capsular bag after the removal of the nuclear material. Presently, viscoelastic material is inserted into the capsular bag to expand the capsular bag so that the implant lens can be slid inside the bag. Without the use of such viscoelastic material, the capsular bag tends to collapse on itself and it then becomes very hard to place the implant lens precisely within the envelope of the capsular bag. The viscoelastic material is quite expensive and even if the shield does not completely eliminate the use of such viscoelastic material, the shield will reduce the amount of the material necessary to maintain the capsular bag open. The shield, therefore, facilitates a placement of the intraocular lens thereby reducing or eliminating the need for viscoelastic material.

The use of the shield for the present invention changes the current surgical procedure in that, at present, the nucleus is removed first and then the cortical material is aspirated. Although there have been some isolated reports of surgeons removing first a small amount of cortical material in order to reduce the volume of this material to enhance the removal of the nucleus, this represents only a small deviation from standard extracapsular cataract surgery. In the present invention, a substantial portion if not substantially all of the cortical material is removed first to allow for the placement of the shield in position. Specifically, in the present invention, the cortical material is aspirated initially. This reduces the endocapsular volume to allow room for the placement of the shield so that the shield can be positioned between the nucleus and the posterior capsular bag.

The shield device of the present invention may be further designed to form an envelope so that there is both an anterior as well as a posterior leaf for the shield. If a shield of this type is used, it would protect not only the posterior capsule, but would also protect the corneal endothelium which is an internal cellular lining formed of a single layer of endothelial cells. Damage to this layer of cells may result in permanent clouding and swelling of the cornea. The endothelial cells act like a pump mechanism to return water, which tends to flow from the eye into the cornea, back into the eye. These cells thereby pump water from the cornea back into the anterior chamber. If the cells are damaged, the cornea becomes swollen and this results in pain and loss of vision. Any significant damage to the endothelial cells during a cataract operation can result in permanent loss of corneal clarity as well as pain and may necessitate corneal transplantation.

If the shield is formed as an envelope this further allows the surgeon to perform the entire removal of the nuclear material from within this envelope and thereby protecting both the posterior capsule and the corneal endothelium during removal of the nucleus.

Another potential advantage of an envelope type shield is that the envelope may be used to provide for a simple manual expression of the nucleus or portions of the nucleus. The envelope may essentially form a basket which can be placed around the nucleus and then drawn out of the eye. This could have great value in areas of the world where mechanized equipment for cataract extractions are not available. The envelope would provide a reliable way of removing the nucleus safely while reducing the risk of endothelial damage as well as reducing the risk of capsular rupture.

A clearer understanding of the present invention will be had with reference to the following description and drawings.

BRIEF DESCRIPTION OF THE DRAWINGS

FIGS. 1(a)–1(f) illustrate a plurality of different shapes for the capsular shield of the present invention;

FIGS. 2(a)–2(c) illustrate combinations of shapes for the capsular shield of the present invention;

FIGS. 3(a) and 3(b) illustrate the use of positioning holes that may be used with any of the shapes of FIGS. 1 and 2;

FIGS. 19(a)–19(f) illustrate the use of the capsular shield formed as an envelope to remove the nuclear material out of the eye.

DETAILED DESCRIPTION OF THE PREFERRED EMBODIMENTS

Figure 4A:
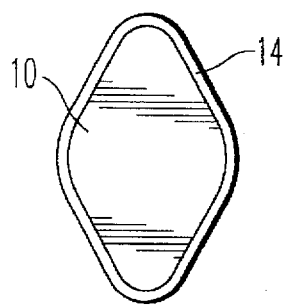
FIGS. 4(a)–4(h) illustrate a number of ways in which the capsular shield may include a variety of support structures.
Figure 4B:
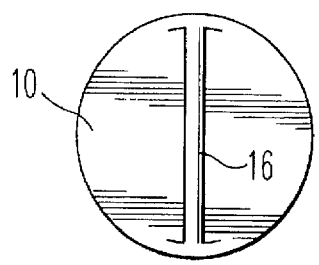
Figure 4C:
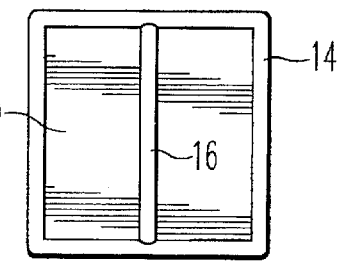
Figure 4D:
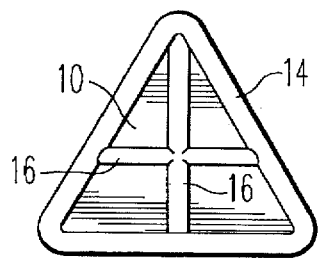
Figure 4E:
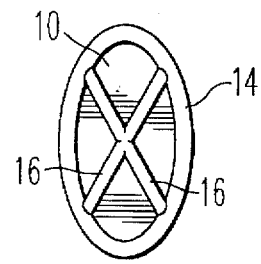
Figure 4F:
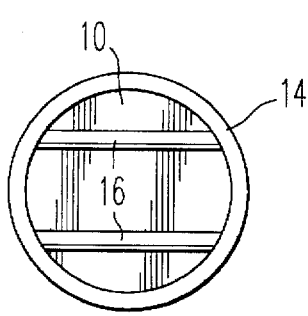
Figure 4G:
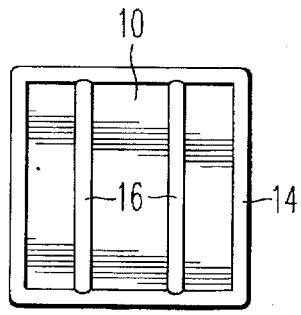
Figure 4H:
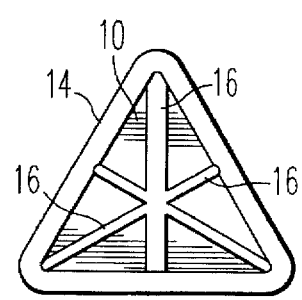

The capsular shield of the present invention may be formed of a variety of different materials. Specifically, the shield may be formed of any suitable material such as a soft plastic or even a hard plastic which is flexible. For example, the shield may be formed of silicone, collagen, or even a hydro gel material. In addition, any of the materials that are currently used to form intraocular lenses may be used as long as the material is flexible enough to be inserted and removed. Further, the shield may be formed of a gelatinous type of substance so that the shield may be removed by aspiration. Alternatively, the shield may be formed by a viscous or gel-like substance which is injected between the nucleus and the posterior capsule. The substance would then assume a more solid state form to create a molded cast between the nucleus and the posterior capsule. The substance may be temperature sensitive such as thermoplastic or thermosetting or may be a two part composition with one part acting as an actuator to form the more solid form. In any event, a typical material may be for example, silicone, since this material is widely used in medical practice for permanent and temporary implantation in the human body.

FIGS. 1(a)–1(f) show a variety of shapes that the capsular shield of the present invention may take and, as a convenience, a common reference numeral 10 is used to refer to any of the capsular shields described in this application no matter what its shape. As can be seen in FIG. 1, various shapes for the shield 10 encompass various configurations including ephlel, oval, circular, square, rectangular and triangular.

As shown in FIG. 2, in addition to the generalized shapes shown in FIGS. 1(a)–1(f) the capsular shield 10 may also be formed to have shapes which are combinations of the shapes shown in FIGS. 1(a)–1(f) and for illustrious purposes only FIGS. 2(a)–2(c) illustrate three such combinations.

In order to provide for the positioning of the capsular shield within the eye, as will be described later, the capsular shield 10 may also include positioning holes 12 as shown by two examples in FIGS. 3(a) and 3(b). The holes 12 may either be located at two ends of the shield or may be located at positions around the circumference of the shield.

It may also be desirable to provide for a greater stability in the capsular shield than that provided by a uniform thickness member. To that regard, the capsular shield of the present invention may include a variety of circumferential ridges and/or ribs to provide internal support. This is shown in FIGS. 4(a)–4(h) and includes the circumferential ridges 14 and internal ribs 16.

Figure 5A:
FIGS. 5(a)–5(c) illustrate the cross-section of a typical capsular seal and its elastic memory.
Figure 5B:
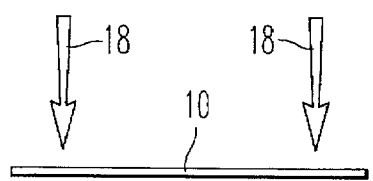
Figure 5C:
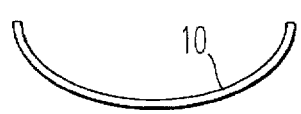

In order to enhance the insertion and removal of the capsular shield of the present invention, it is desirable that the shield have an elastic memory so that it normally has a C-shaped cross-sectional configuration. This is shown in FIGS. 5(a)–5(c). The capsular shield 10 is first shown in FIG. 5(a) to have the C-shaped cross-section. In FIG. 5(b) the shield is shown to be flattened by forces shown by arrows 18. The shield 10 may then recover to a substantially C-shaped cross-section, as shown in FIG. 5(c) when the forces are removed. This type of structure is generally defined as an elastic memory so that the shield 10 may be flattened before insertion, but will resume its C-shaped configuration during and after insertion.

The advantage of such a C-shaped configuration is that it helps to reduce forces against the capsule during insertion of the shield 10 and helps to prevent injury to the capsule by the shield after insertion. This is because the leading end of the shield 10 will tend to curl anteriorly towards the denser material both during and after insertion. The nuclear material will thereby resist the anterior force of the shield and cause a shield to follow the contour of the nuclear material rather than allow the shield 10 to push against the posterior capsule.

Figure 6A:
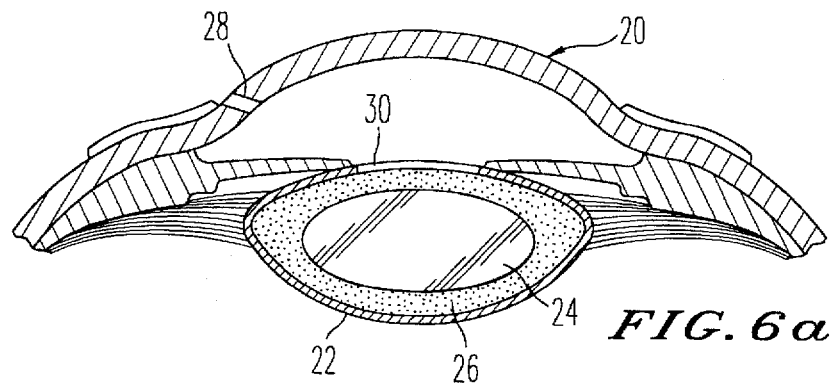
FIGS. 6(a)–6(d) illustrate in general the structure of the eye and the method of insertion of the capsular shield before removal of the lens capsule.

The above advantage of the C-shaped shield with an elastic memory can be further seen with reference to FIGS. 6(a)–6(d) which illustrate in general the insertion of the capsular shield into the eye. As shown in FIG. 6(a), the eye 20 includes a capsule 22 which contains a nucleus of dense material 24 surrounded by softer cortex material 26. During the cataract surgery a small scleral or corneal incision 28 is made through the exterior of the eye to gain access to the interior and a circular opening 30 is formed in the anterior portion of the capsule 22.

Figure 6B:
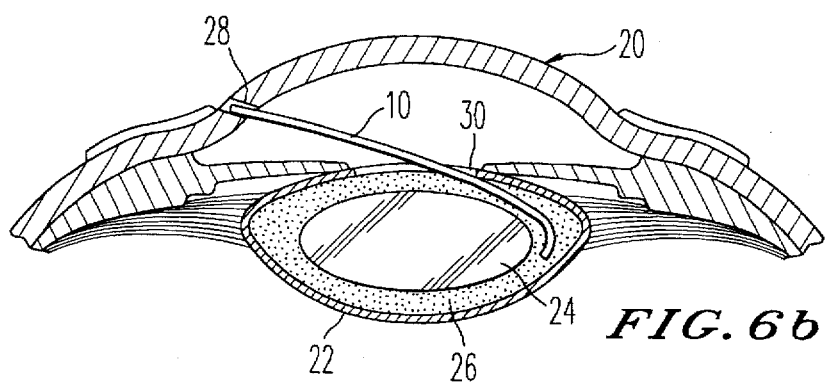
Figure 6C:
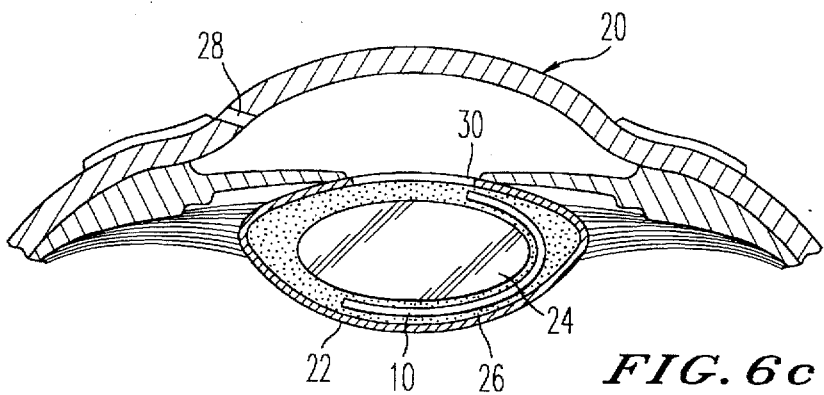
Figure 6D:
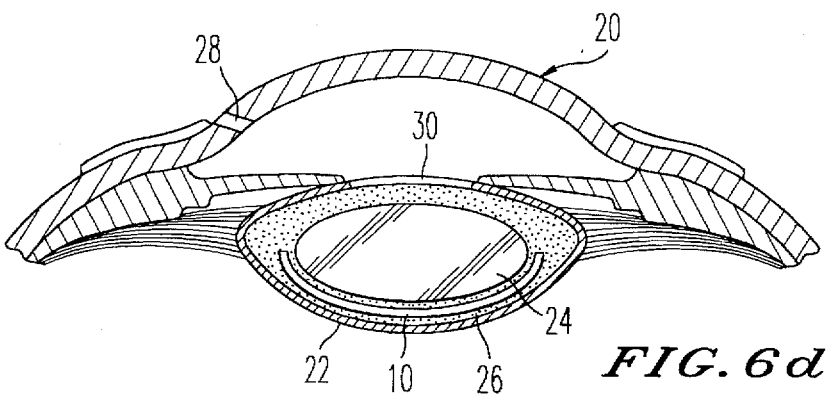

As shown in FIG. 6(b), the capsule shield 10 may be inserted through the openings 28 and 30 to curl around the dense nucleus 24. The shield 10 will follow the nucleus 24 as the capsule shield is further inserted, as shown in FIG. 6(c). With complete insertion, the capsule shield 10 lies between the nucleus 24 and the posterior wall of the capsule 22 as shown in FIG. 6(d). Again, because of the C-shaped curl of the shield, the capsule shield 10 tends to follow the contour of the nucleus 24 rather than push against the posterior wall of the capsule 22.

Figure 7A:
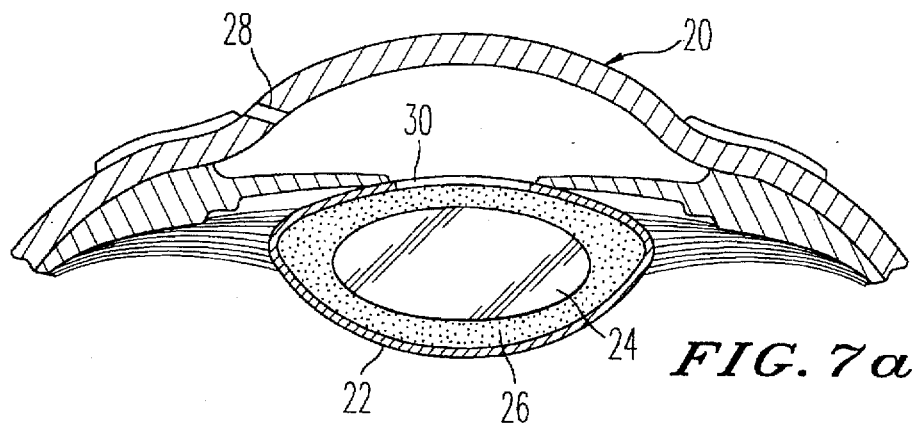
FIGS. 7(a)–7(f) illustrate in more detail the surgical technique for manual insertion of the shield.
Figure 7B:
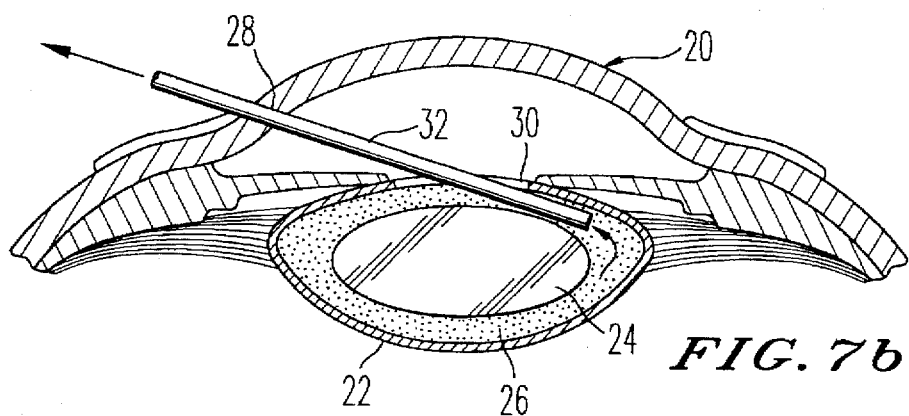

As a specific surgical technique, it is probably desirable to remove a substantial portion if not substantially all of the cortex material 26 before insertion of the capsule shield 10. This is shown in FIGS. 7(a)–7(f). In FIG. 7(a), the eye 20 is shown to include the scleral incision 28 and the circular opening 30 which are made as the initial steps in the cataract procedure. The cortex material 26 lies between the nucleus 24 and the capsule 22. As the next step in the surgical procedure as shown in FIG. 7(b), a tool 32 is inserted through the incision 28 and opening 30 so as to aspirate the cortex material 26 which is softer and more gelatinous in consistency than the nucleus 24.

Figure 7C:
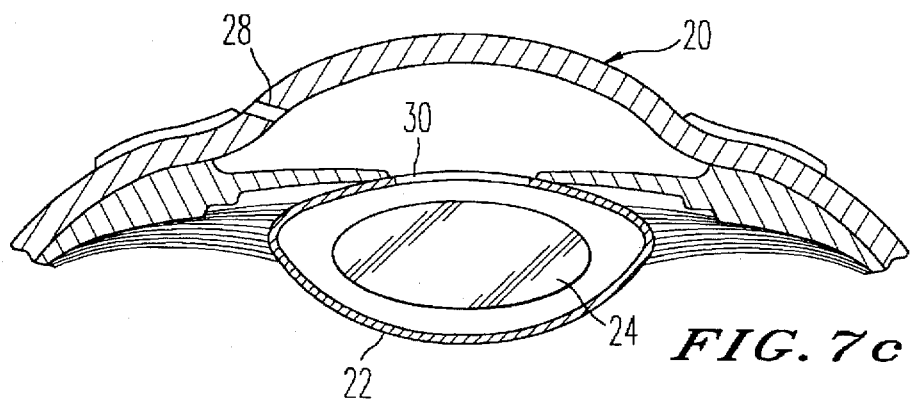
Figure 7D:
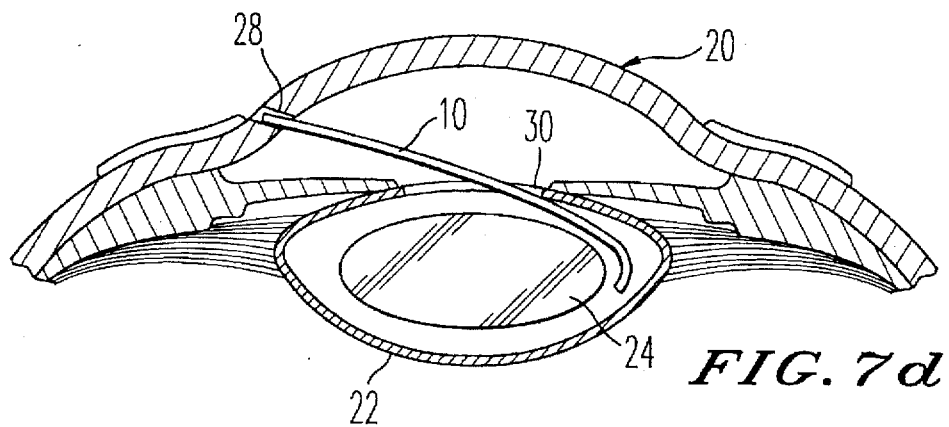
Figure 7E:
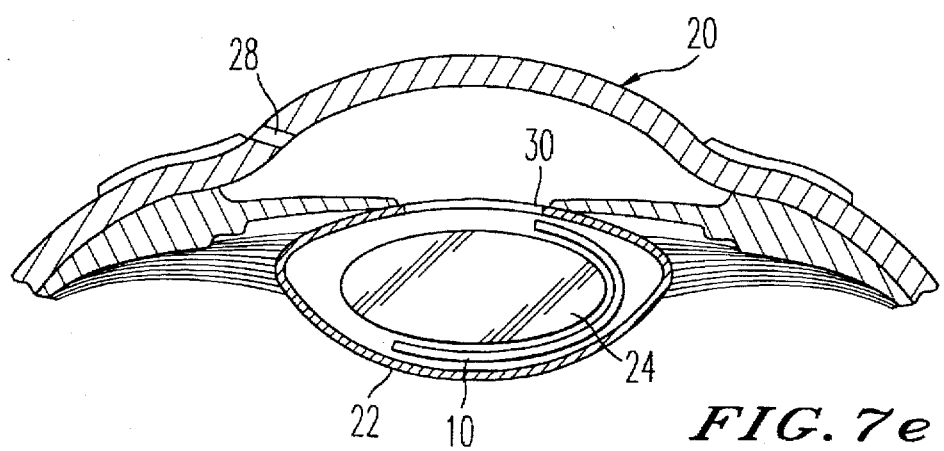
Figure 7F:
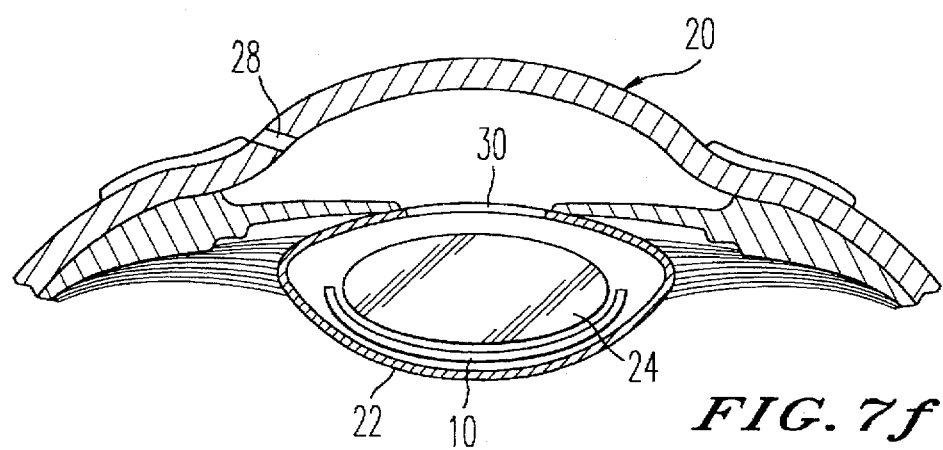

The aspiration therefore provides for the removal of the cortex material 26 to produce the structure shown in FIG. 7(c) wherein a substantial portion of the cortex material 26 has been removed to have the nucleus 24 being loosely contained within the capsule 22. FIGS. 7(d)–7(f) then shown the insertion of the capsule shield 10 through the incision 28 and opening 30 using for example, manual techniques such as with forceps. Since the cortex material 26 has been removed, this creates a reduction in volume of the endocapsular contents to create the space between the nucleus 24 and capsule 22 as shown in FIG. 7(c) and this space allows for a much simpler placement of the capsular shield 10.

Once the capsular shield 10 is in place as shown in FIG. 7(f), the nucleus 24 may then removed with any of the techniques current being used or described in the literature, including mechanical, ultrasonic, sonic shockwave, electro mechanical, or laser removal. The positioning of the shield as shown in FIG. 7(f) protects the posterior capsule from being opened inadvertently during the removal of the nucleus 24.

Figure 8A:
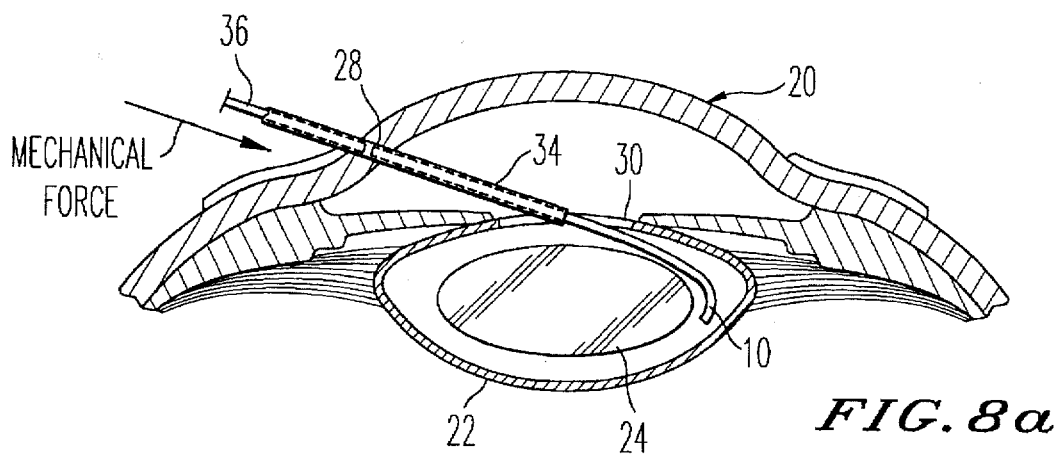
FIGS. 8(a)–8(c) illustrate a further insertion technique using a cylindrical insertion device.
Figure 8B:
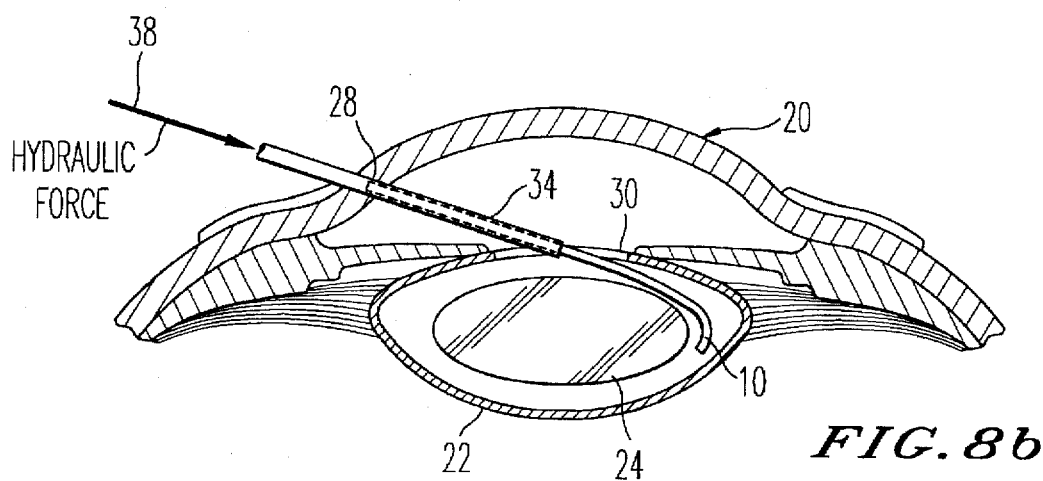

FIGS. 8(a) and 8(b) illustrate a further alternate technique for inserting the capsular shield 10 once the cortex material 26 has been removed. Specifically, the capsule shield 10 may be placed between the capsule 22 and the nucleus 24 using a cylindrical insertion device 34. The shield 10 is advanced through the cylindrical insertion device 34 and into the capsule 22 using either a mechanical probe 36 as shown in FIG. 8(a) or by a hydrodynamic force as shown by the arrow 38 in FIG. 8(b).

The probe 36 may be a rigid member which pushes the shield out of the cylinder and into the capsule. The hydrodynamic force may be provided by a viscoelastic material which is located within the cylindrical insertion device 34. Compression of the viscoelastic material within the cylindrical device 34 using, for example, a plunger or screw device produces the hydrodynamic force 38 which will propel the shield into the desired location within the capsule 22 as shown, for example, in FIG. 7(f). The cylindrical insertion device 34 may be anyone of the types currently used to insert foldable intraocular lenses.

Figure 8C:
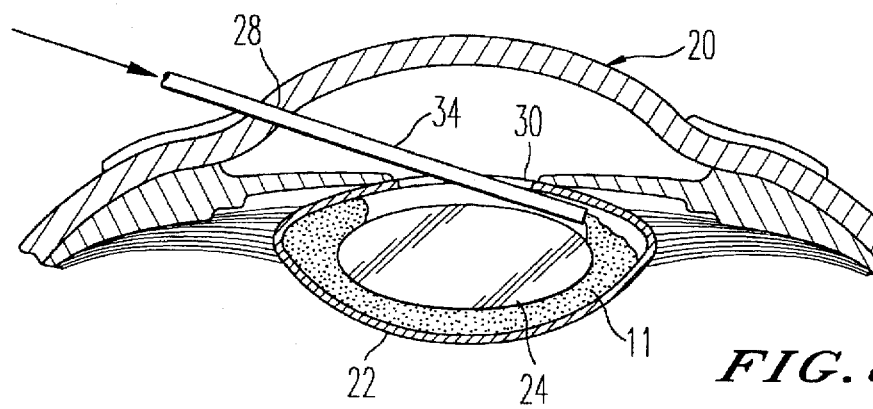
Figures 9A, 9B, 9C, 9D:
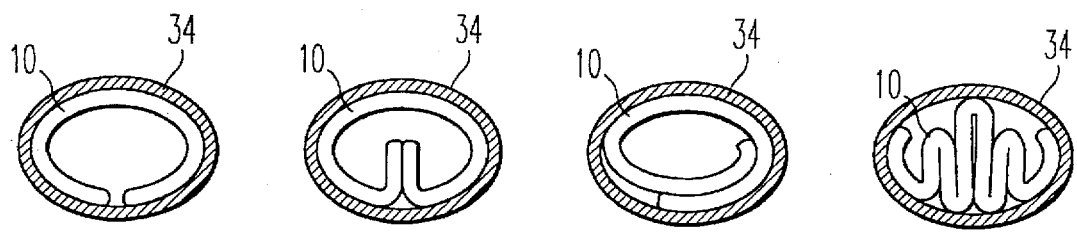
FIGS. 9(a)–9(d) illustrate various ways of compressing the capsular shield within the cylindrical insertion device.

FIG. 8(c) illustrates the use of the insertion device 34 for injecting a viscous or gel-like substance 11 between the nucleus 24 and posterior capsule. This substance 11 will harden to form a more solid state harden by temperature or by chemical reaction.

FIGS. 9(a)–9(d) illustrate how the shield 10 may be rolled or compressed within the cylindrical device 34 to facilitate the insertion of the capsular shield 10 through a small incision and specifically the small scleral incision 28 shown in FIGS. 8(a) and 8(b). It is to be appreciated that the capsular shield 10 can be compressed in other ways other than those shown as examples in FIGS. 9(a)–9(d).

After the nucleus 24 has been removed then the capsular shield 10 would normally also be removed and two techniques for accomplishing this result are shown in FIGS. 10 and 11. It is to be appreciated that normally an intraocular lens will have been inserted but for ease of understanding the removal of the capsule shield 10 is first described without illustrating an intraocular lens in position.

Figure 10A:
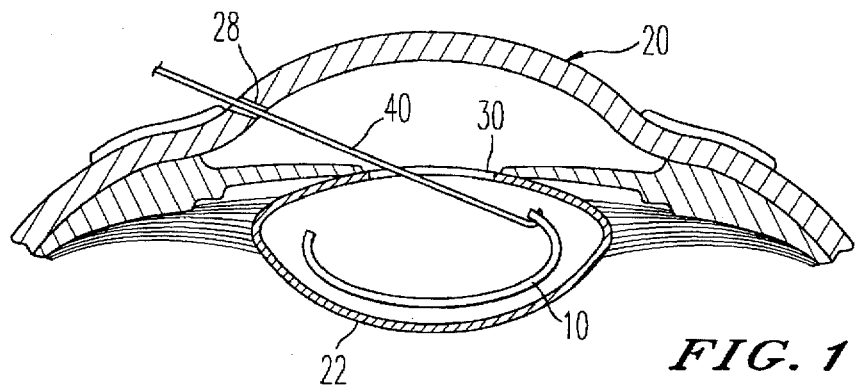
FIGS. 10(a)–10(c) illustrates the technique for removing the capsular shield after removal of the cataract and using a hook or forceps.
Figure 10B:
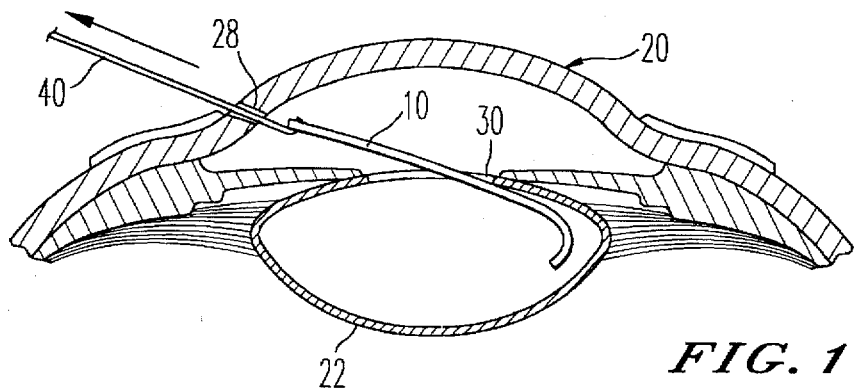
Figure 10C:
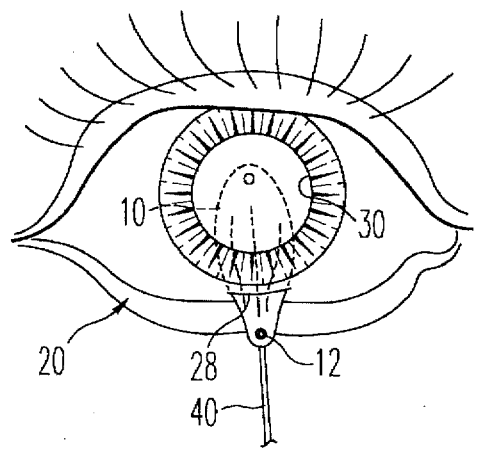

As shown in FIG. 10(a)–10(c), the capsule may be removed by a mechanical device such as a probe with a hook at the end to engage an opening 12 in the capsular shield as shown in FIGS. 3(a) and 3(b). The probe is inserted through the incision 28 and through the opening 30 in the capsule 22 to hook the end of the capsular shield 10 so that the shield may be pulled out of the capsule 22. As shown in FIG. 10(c), as the capsule shield 10 is removed, the shield 10 tends to fold or compress to become deformed, which allows the removal of the shield through the incision 28 which is normally smaller than the width of the shield 10. Again, this is because of the flexible, deformable material from which the shield is formed which allows the shield 10 to collapse and fold or compress to a smaller size.

Although FIGS. 10(a)–10(c) have been illustrated with a hook-like instrument positioned within a hole in the shield 10, it is to be appreciated that the instrument may actually operate not in a hole but against a ridge, such as the ridges 14 in FIG. 4, and with the positioning of the hook against the ridge allowing for the removal of the shield 10 from the eye. Additionally, in place of a hook-like instrument, a pair of forceps may be used to grasp the end of the shield 10 and thereby withdraw the shield 10 through the incision 28 and out of the eye.

Figure 11A:
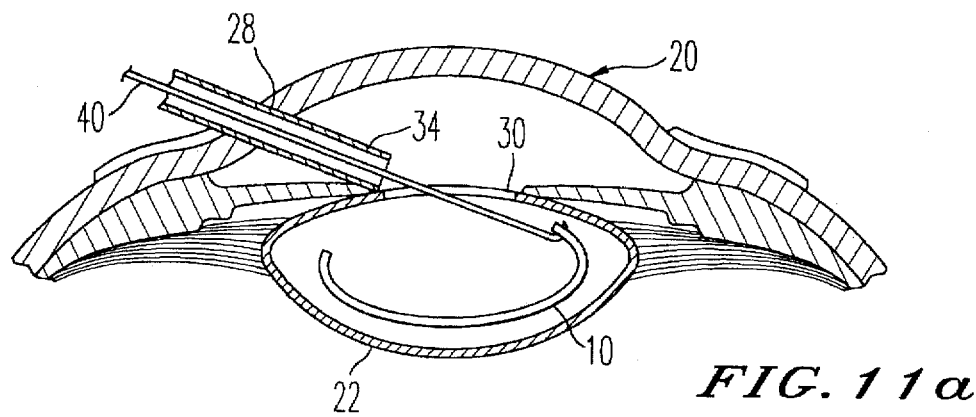
FIGS. 11(a)–11(c) illustrates the removal of the capsular shield using a cylindrical guide.
Figure 11B:
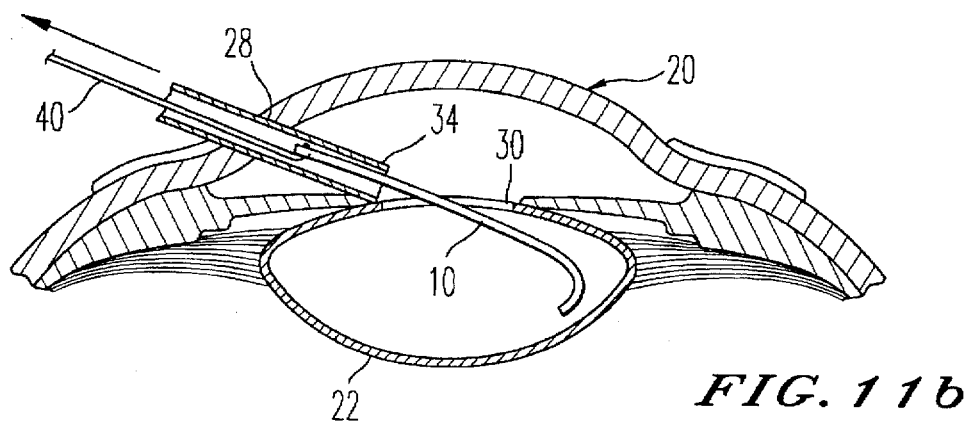
Figure 11C:
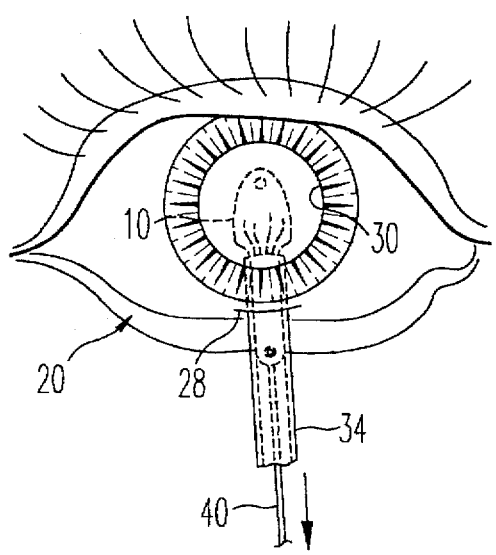

As a further technique for removing the shield from within the eye, the cylindrical guide 34 as shown in FIG. 8 or a similar cylindrical guide may be used not only for insertion but also for withdrawal. FIGS. 11(a)–11(c) illustrate this technique. The cylindrical guide 34 is passed through the incision 28 and opening 30 into the interior of the eye and with an instrument, such as the hook-like instrument 40, inserted through the cylindrical guide to engage the end of the shield 10. The instrument 40 is then withdrawn thereby pulling the shield and with the cylindrical device 34 forcing the shield 10 to fold, curl, compress and deform into the cylindrical device. The shield 10 is then drawn out of the eye through the cylinder and through an incision 28 smaller than the width of the shield 10.

It was previously indicated that the shield 10 may be formed of a gelatinous material. With such a material it may not be necessary to use any mechanical devices to remove the shield since the shield could be removed by aspirating the gelatinous material through a cannula. It is also to be appreciated that the shield may also be made of material which is compatible within the eye and as such, the shield may be left in position within the eye and act as a capsule bag maintainer for easier insertion of an intraocular lens or may even be left in position after the insertion of an intraocular lens as a further support for the capsular bag.

Figure 12A:
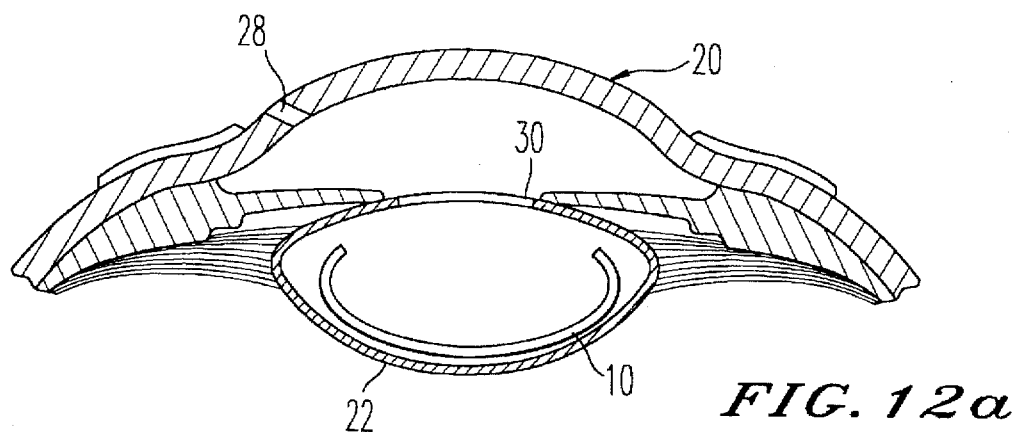
FIGS. 12(a)–12(c) illustrates using the capsular shield to maintain the capsular bag open.
Figure 12B:
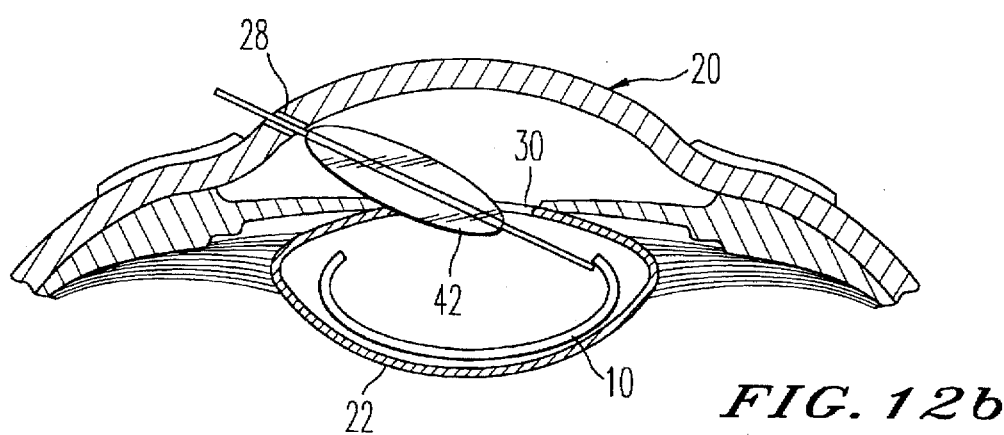
Figure 12C:
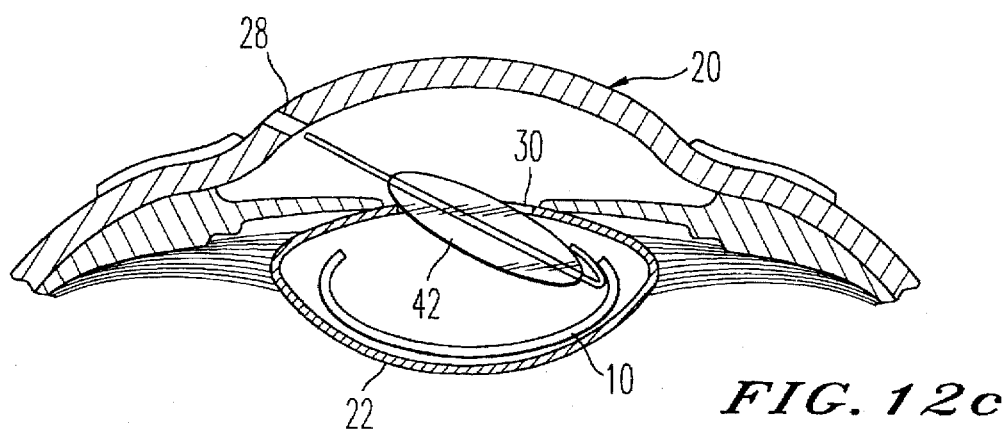

FIGS. 12(a)–12(c) illustrates how the shield 10 serves as a capsule bag maintainer. Specifically, the shield maintains the shape of the capsule bag so as to facilitate placement of an intraocular lens of any of the known types. As shown in FIG. 12(a), the shield 10 has been positioned within the capsule 22 and because of the C-shaped configuration of the shield 10, the capsule bag is held in an open position to maintain the interior volume of the bag 22. In FIG. 12(b), an intraocular lens 42 is shown to be initially inserted through the incision 12 and the opening 30 and to be partially within the bag 22. The shield 10 keeps the bag 22 open to facilitate a reliable positioning of the intraocular lens inside the capsular bag 22. FIG. 12(c) illustrates the lens 42 almost in its final position within the capsular bag 22 which is being maintained open by the shield 10.

Figure 13A:
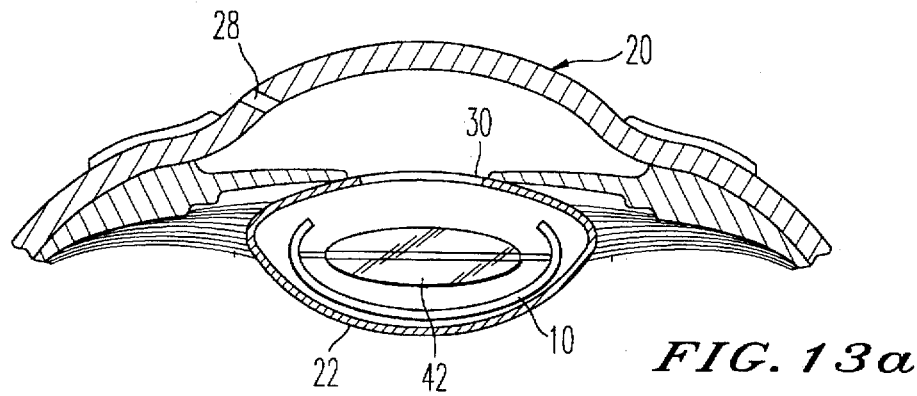
FIGS. 13(a)–13(e) illustrates the removal of the capsular shield after the placement of the intraocular lens.
Figure 13B:
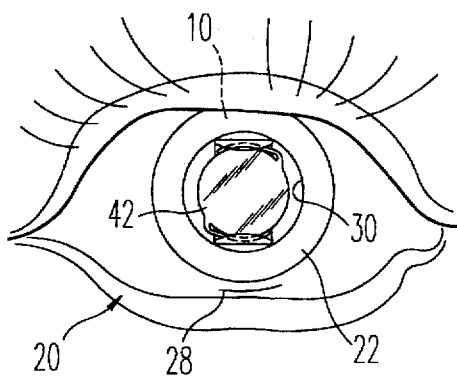
Figure 13C:
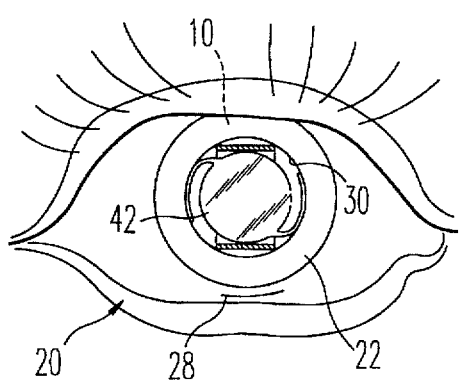
Figure 13D:
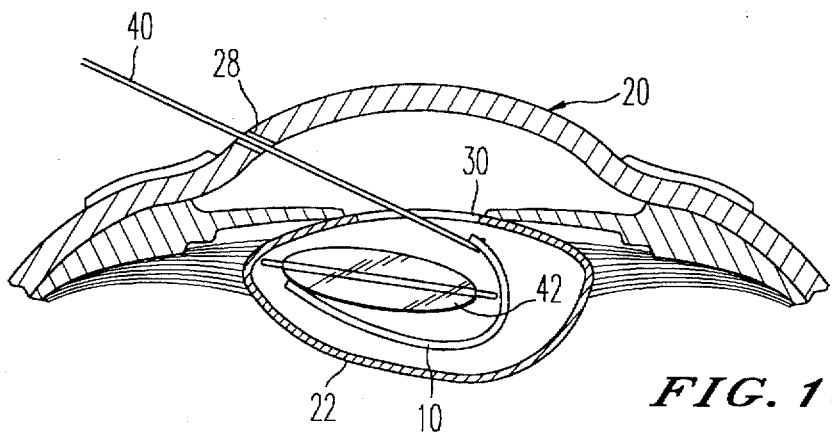
Figure 13E:
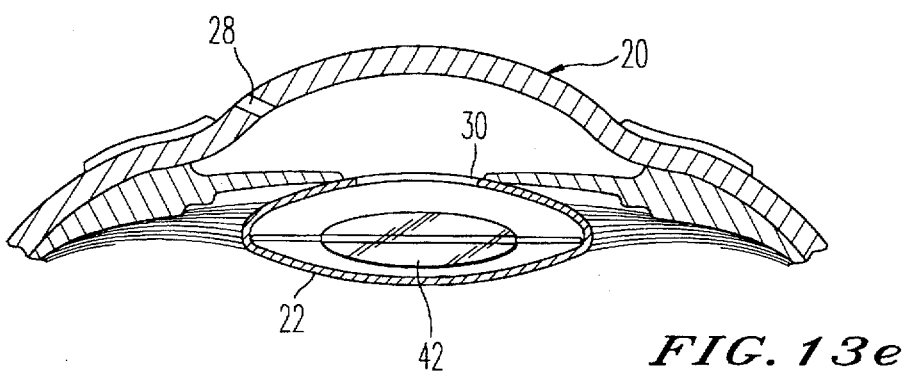
Figure 14A:
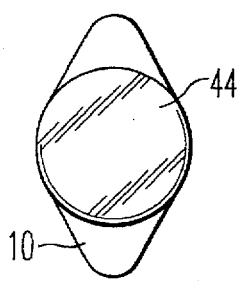
FIGS. 14(a)–14(m) illustrate various shapes for the capsular shield with the shield also serving as an intraocular lens and with FIGS. 14(a)–14(i) illustrating various shapes for the capsular shield and FIGS. 14(j)–14(m) showing cross-sectional views.
Figure 14B:
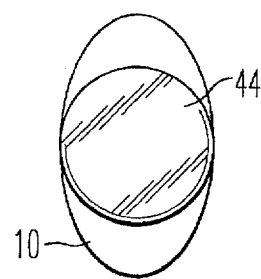
Figure 14C:
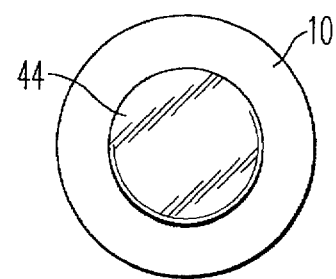
Figure 14D:
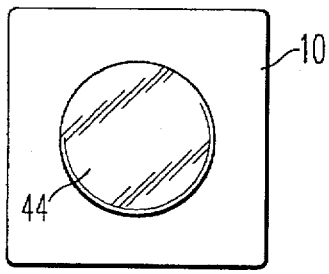
Figure 14E:
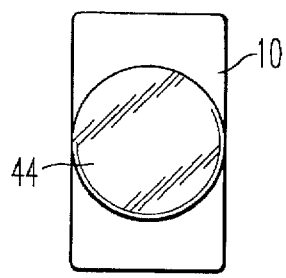
Figure 14F:
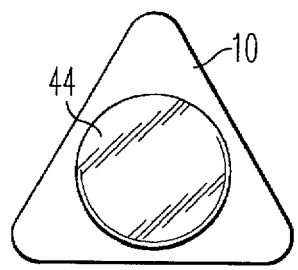
Figure 14G:
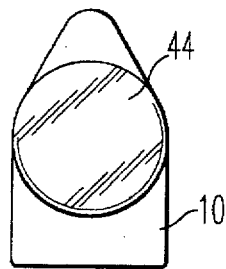
Figure 14H:
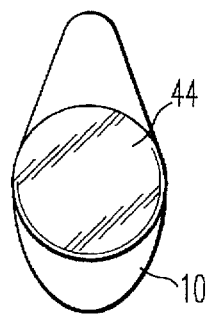
Figure 14I:
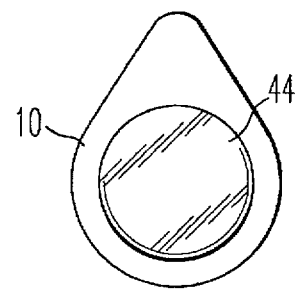
Figure 14J:
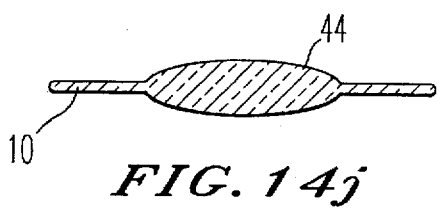
Figure 14K:
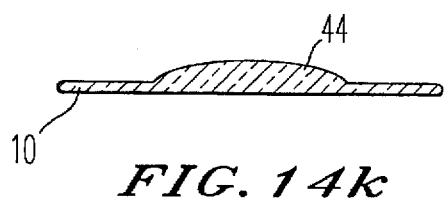
Figure 14L:
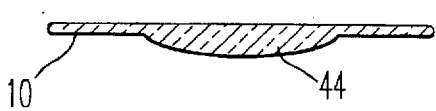
Figure 14M:
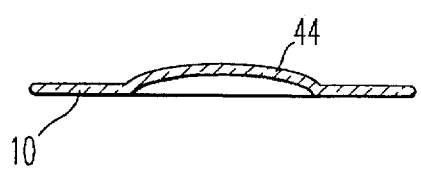

FIGS. 13(a)–13(e) illustrate the intraocular lens 42 in position and show the technique for removing the shield 10 with the lens in position. FIG. 13(a) illustrates a cross-sectional view of the eye 20 with the intraocular lens 42 in position and with the shield 10 surrounding the lens 42. FIG. 13(b) illustrates an anterior view of FIG. 13(a) to show the positioning of both the lens 42 and shield 10 within the capsular bag. FIG. 13(c) is a further anterior view of the capsule 22, but cut away to show the intraocular lens 42 positioned within the capsule 22 and with the shield 10 located between the lens 42 and the posterior capsule 22. FIG. 13(d) illustrates the initial removal of the shield 10 using the hook-like instrument 40 and with the shield 10 pulled over the lens 42. As the shield 10 is being removed, it can be seen that the capsule 22 starts to collapse around the intraocular lens 42. If necessary, an additional instrument, such as a blunt specula, may be placed over the intraocular lens 42 to provide a gentle downward pressure against the intraocular lens so that the intraocular lens 42 will be held in position as the shield 10 is removed. Finally, as shown in FIG. 13(e) the shield 10 has been removed and as shown the capsule bag 22 tends to collapse around the intraocular lens 42.

As an alternative to the use of a shield 10 and an intraocular lens 42, the shield 10 may include a central portion to provide diopter power so that the shield may function not only as a shield but also as an intraocular lens. This structure is shown in FIGS. 14(a)–14(m) and as illustrated there is a shield portion 10 and a lens portion 44. A variety of configurations for this combined shield/lens is shown in FIGS. 14(a)–14(i) and with a variety of dioptric powers provided by the central lens portion 44. Specifically, the diopter power may be provided by the central portion having both surfaces convex as shown in 14(j), plano convex surfaces, as shown in 14(k) and 14(l) and convex concave surfaces, as shown in 14(m). If the shield 10 includes the lens portion 44, then it is apparent that after insertion of the shield/lens and removal of the nucleus, the cataract procedure is essentially complete.

Figure 15A:
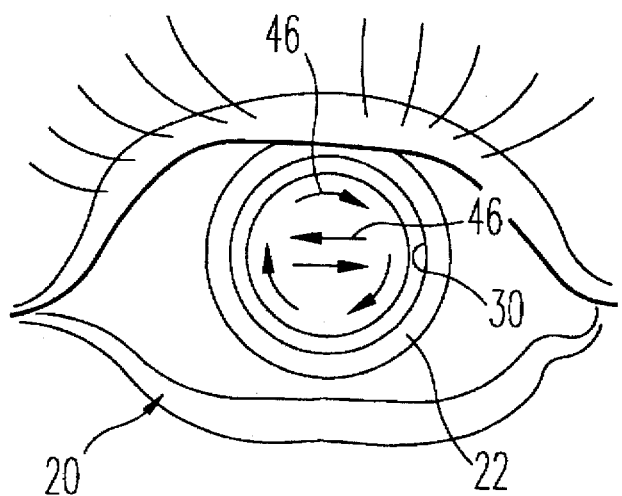
FIGS. 15(a) and 15(b) illustrate the use of the capsular shield as a polishing device.
Figure 15B:
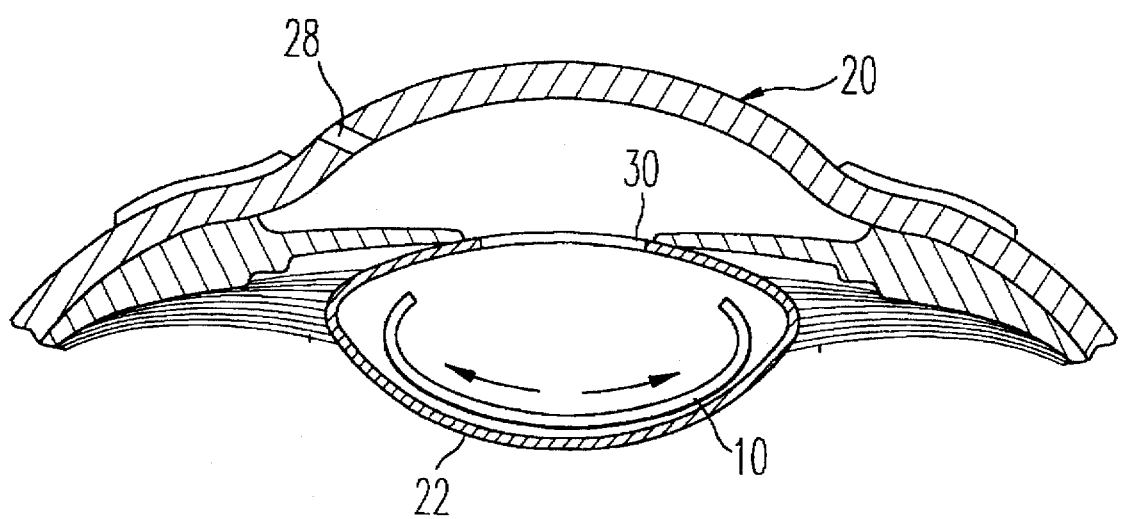

One further advantage of the capsular shield of the present invention is that the shield may be used as a device to polish the posterior capsule to remove epithelial cells and fibrocytes. The removal of these materials reduces the incidence, or may prolong the onset, of post operative posterior capsular opacification. This procedure is illustrated in FIGS. 15(a) and 15(b). As shown by arrows 46, the shield 10 may be rotated clockwise and/or counter clockwise and from side to side to gently scrub or polish the posterior capsule after cortical aspiration. At the present time, the removal of the epithelial cells and fibrocytes is accomplished with a probe-like instrument with an abrasive or rough tip at the end.

A further design for the capsule shield of the present invention includes formation of the shield to not only protect the posterior capsule, but also to protect the corneal endothelium during the cataract procedure. This is shown in FIGS. 16–18. In addition, FIG. 19 provides a further extension of this envelope design to remove the nucleus.

Figure 16A:
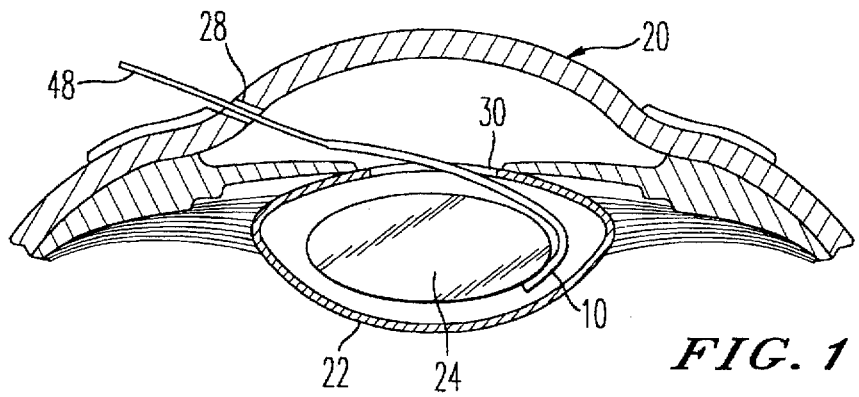
FIGS. 16(a)–16(d) illustrates a design for the capsular shield forming an envelope to additionally protect the corneal endothelium.
Figure 16B:
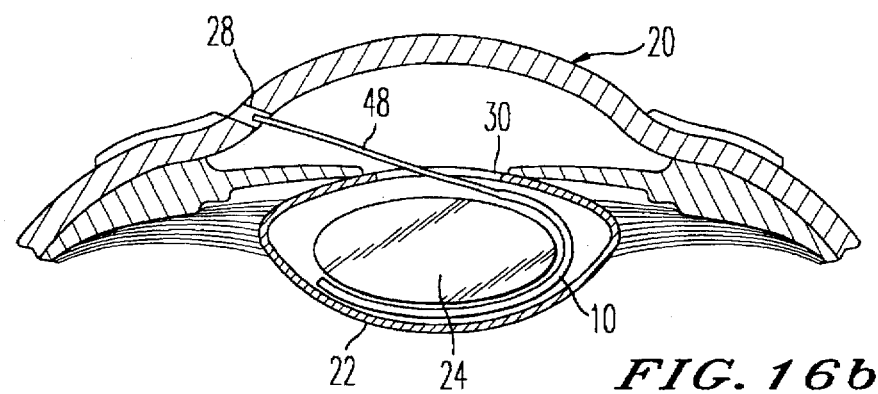
Figure 16C:
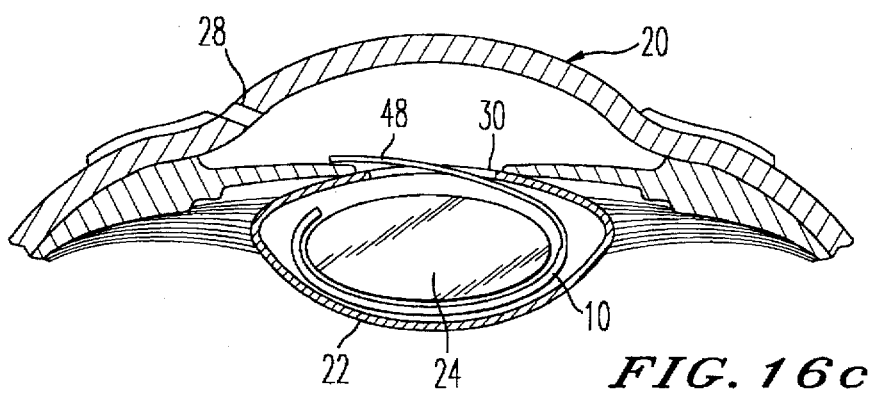

FIGS. 16(a)–16(c) illustrate the insertion of the capsule shield 10 in a manner similar to that shown before. However, the shield 10 includes a further extension or flap 48 that drapes over the anterior portion of the nucleus. This extension 48 of the shield 10 protects the corneal endothelium from damage during cataract removal. In FIG. 16(a), the shield 10 is partially inserted and with the extension 48 being passed through the incision 28. In FIG. 16(b), the shield 10 and the extension 48 are almost completely inserted and FIG. 16(c) illustrates the shield in its position to protect the capsular bag 10 and with the extension 48 draping over the anterior portion of the nucleus.

Figure 16D:
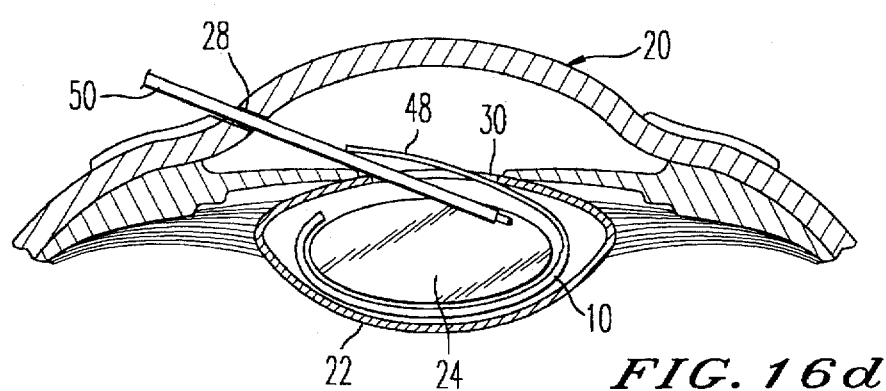

In order to allow the surgeon to continue with the operation, the extension 48 should be made of translucent material so that the surgeon can see through the extension 48 during further surgical procedures. FIG. 16(d) illustrates the shield 10 and extension 48 in position and with a further tool 50 inserted through the incision 28 into the interior of the eye to remove the nucleus 24. The tool 50 may remove the nucleus by any of the known means such as mechanical, acoustic, shockwave, photic, etc. After the nucleus has been removed and an intraocular lens inserted, the extension 48 may be used to provide for the removal of the entire shield 10 since the end of the extension 48 will lie immediately adjacent the incision 28.

Figure 17A:
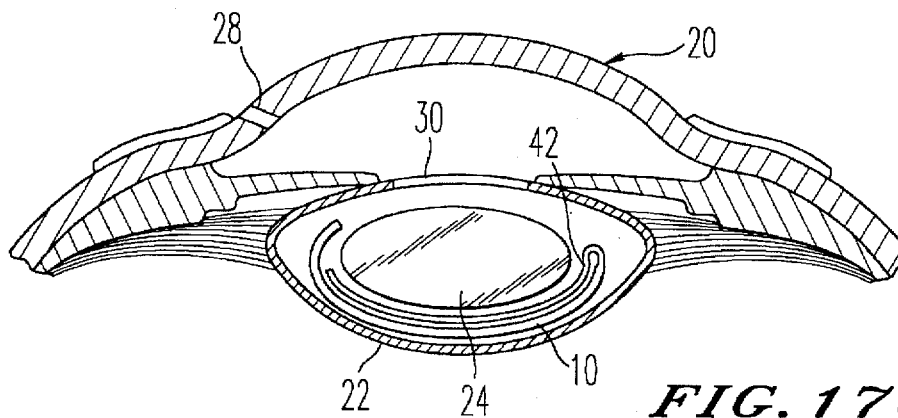
FIGS. 17(a)–17(c) illustrate another capsular shield formed as an envelope.
Figure 17B:
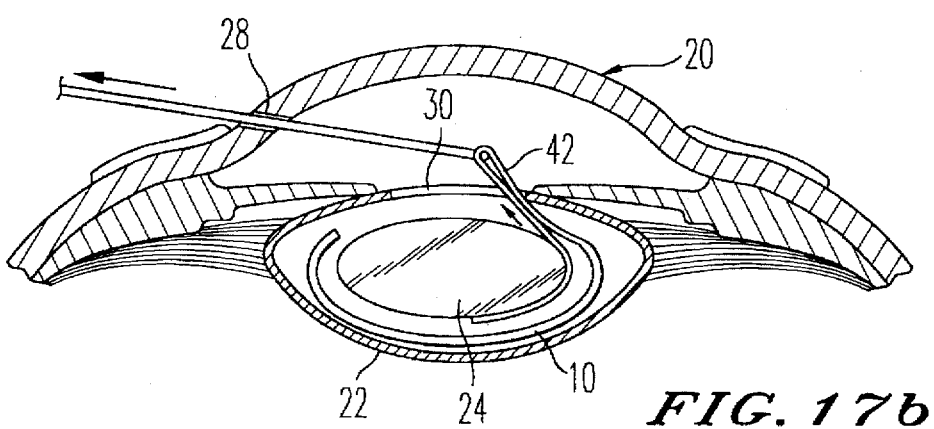
Figure 17C:
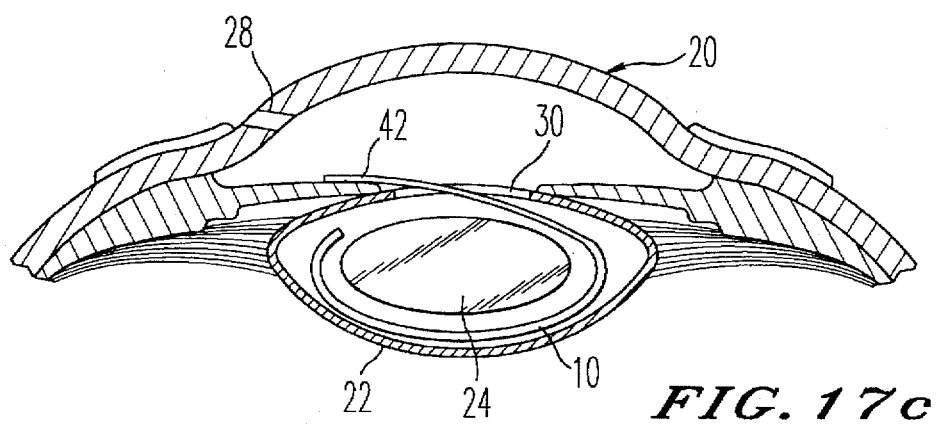
Figure 18A:
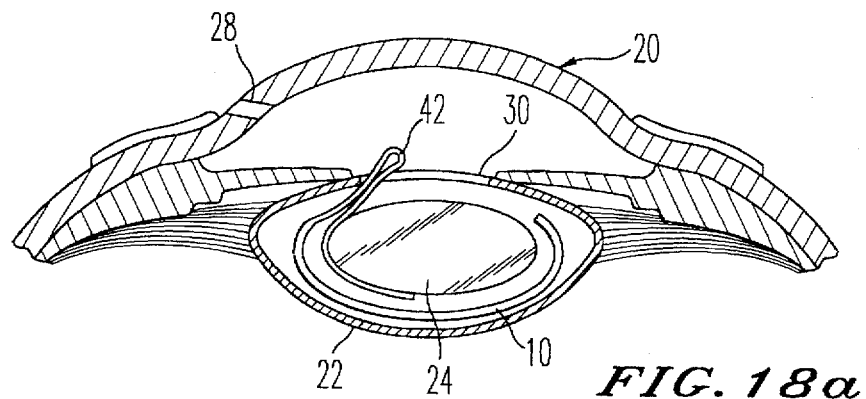
FIGS. 18(a)–18(d) illustrate a further design of the capsular shield formed as an envelope.
Figure 18B:
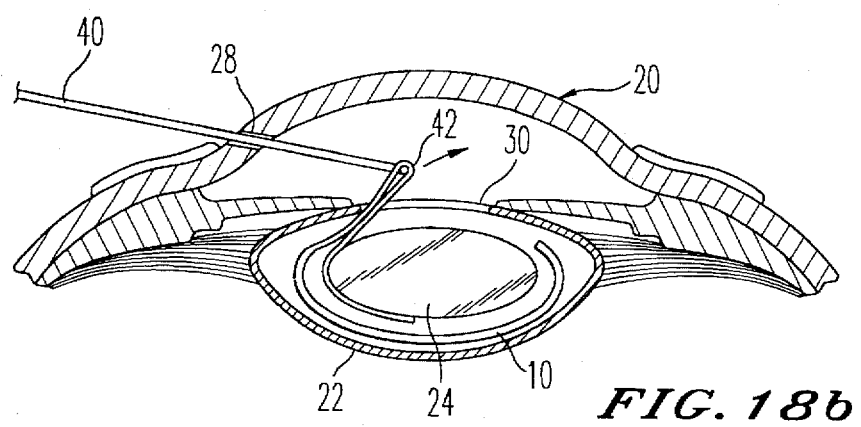
Figure 18C:
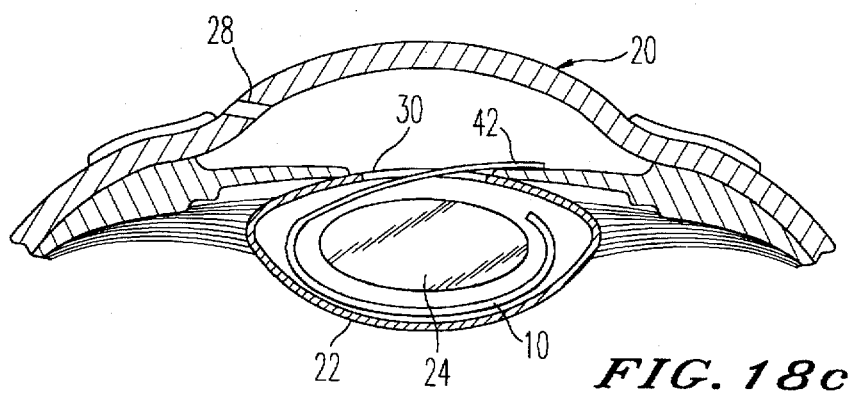
Figure 18D:
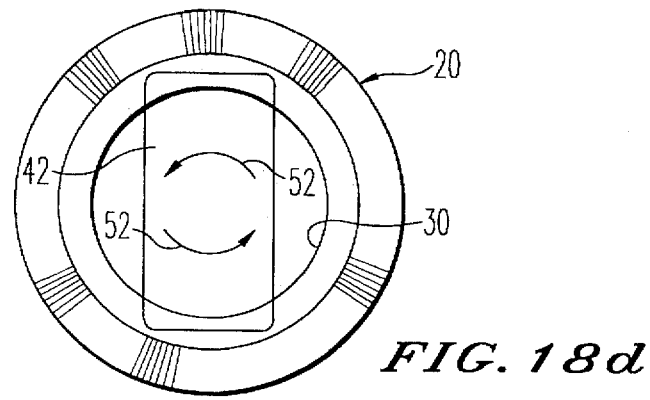

As an alternative to the design for the shield plus extension shown in FIG. 16, the envelope may be folded upon itself as shown in FIGS. 17 and 18. Specifically, as shown in FIG. 17(a)–17(c), after insertion of the combined shield and extension or flap 42, the flap may be pulled out and draped over the anterior surface of the nucleus, as shown in FIG. 17(c). The position of the extension or flap 42 may be as shown in FIG. 17 or may reversed as shown in FIG. 18. If the position is reversed as shown in FIG. 18, once the flap has been pulled out and draped over the anterior surface of the nucleus then the shield must be rotated. This is shown by arrows 52 in FIG. 18(d) so that the orientation of the flap is proper to allow for insertion of the proper tools for removal of the nucleus 24.

The use of an envelope type of design for the shield has a further advantage in that the envelope may form a basket to contain the nucleus so that both the nucleus and shield can be drawn out of the eye at the same time. This may provide a simple way of extracting the nucleus out of the eye reliably and safely while reducing risk of endothelial damage as well as risk of capsular rupture in areas in the world where mechanized equipment for cataract extraction is not available. This technique is shown in FIGS. 19(a) through 19(f).

Figure 19A:
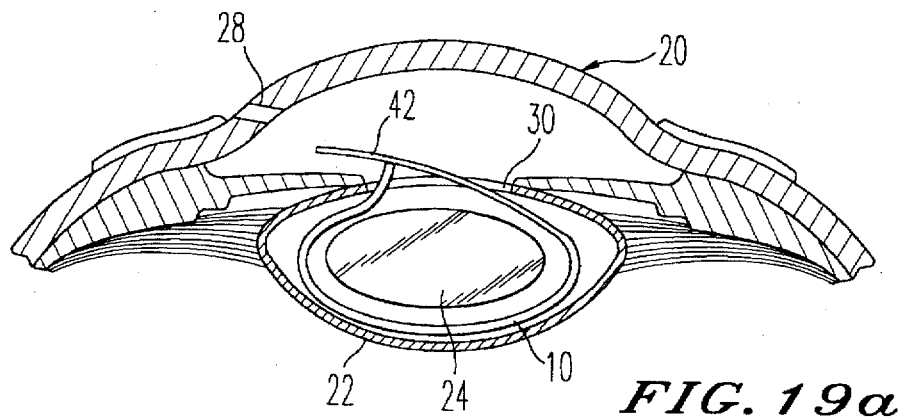
Figure 19B:
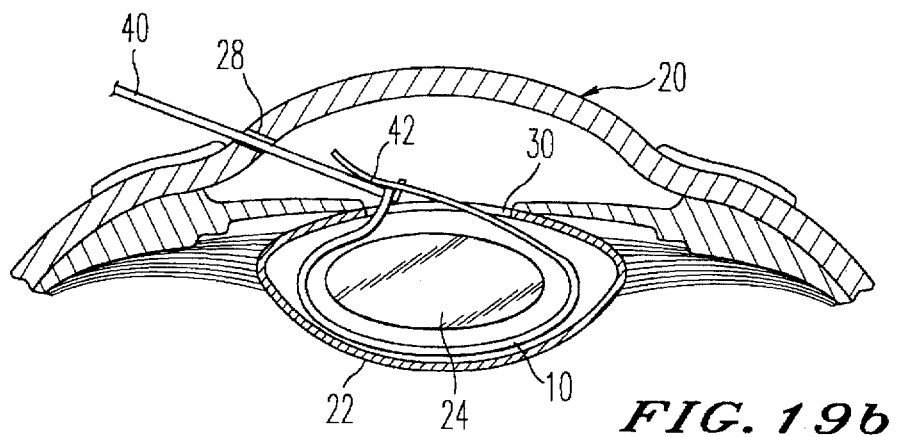
Figure 19C:
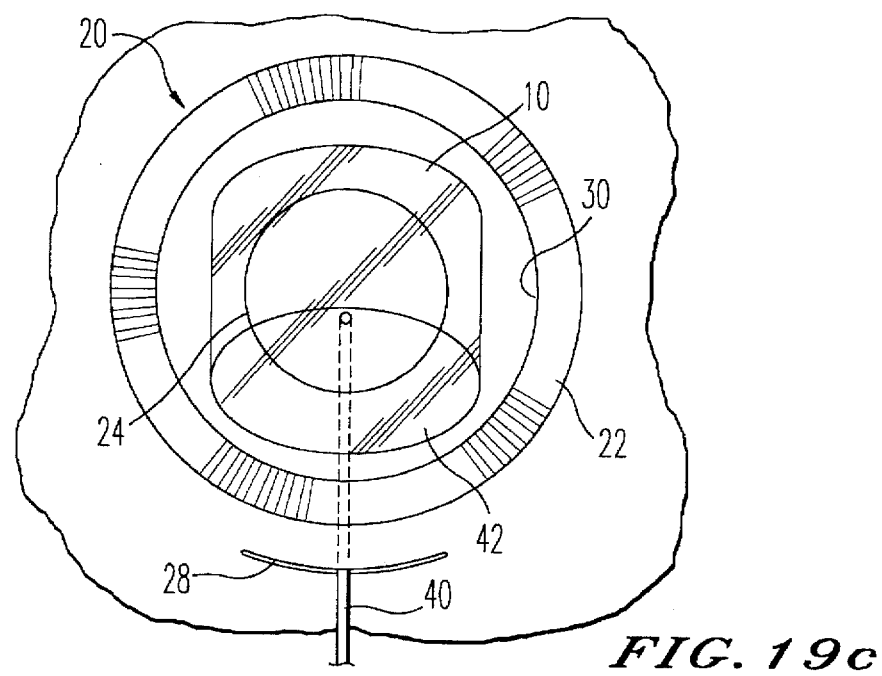

As shown in FIG. 19(a), the shield 10 forms a posterior flap while the extension portion 42 forms an anterior flap which together form a basket to contain the nucleus 24. The hook-like instrument may engage both the anterior and posterior flaps 10 and 42. As shown in FIGS. 19(b) and 19(c), the basket starts to remove the whole nucleus 24. As shown in FIGS. 19(d) and 19(e), the basket continues to remove the entire nucleus 24. Finally, the basket formed by the anterior and posterior flaps completely removes the nucleus, as shown in FIG. 19(f). The envelope formed by the two flaps therefore carries the nucleus out of the eye in a simple and reliable manner.

It can be seen therefore that the capsular shield of the present invention provides for a host of important advantages for cataract surgery.

Although the invention has been described with reference to particular embodiment, it is to be appreciated that various adaptations and modifications may be made and the invention therefore is only to be limited by the appended claims.

I claim:

1. A method of protecting a posterior lens capsule during removal of a lens nucleus, including the following steps, providing a flexible, deformable shield having an outer configuration of a size and shade to fit within the lens capsule at a position between the nucleus and the posterior capsule and to cover a substantial portion of the posterior capsule, inserting the shield into the lens capsule and into a position between the nucleus and the posterior capsule to protect the substantial portion of the posterior capsule during later removal of the lens nucleus, and wherein the shield is provided with a C-shape cross section of material having an elastic memory and including the step of flattening the shield prior to insertion and allowing the shield to return to the C-shape configuration during and after insertion to follow the curvature of the nucleus and not push against the posterior capsule.

2. A method of protecting a posterior lens capsule during removal of a lens nucleus, including the following steps, providing a flexible, deformable shield having an outer configuration of a size and shape to fit within the lens capsule at a position between the nucleus and the posterior capsule and to cover a substantial portion of the posterior capsule, inserting the shield into the lens capsule and into a position between the nucleus and the posterior capsule to protect the substantial portion of the posterior capsule during removal of the lens nucleus, removing the lens nucleus while the lens capsule is protected by the shield, removing the shield from the lens capsule after the removal of the lens nucleus, and wherein the shield is provide with at one opening and additionally providing an instrument with a hook-like end with the additional steps of inserting the instrument into the lens capsule to have the hook-like end of the instrument engage the opening in the shield and removing the instrument and shield from the lens capsule by withdrawing the instrument.

3. A method of protecting a posterior lens capsule during removal of a lens nucleus, including the following steps, providing a flexible, deformable shield formed of gelatinous material having an outer configuration of a size and shape to fit within the lens capsule at a position between the nucleus and the posterior capsule and to cover a substantial portion of the posterior capsule, inserting the shield into the lens capsule and into a position between the nucleus and the posterior capsule to protect the substantial portion of the posterior capsule during removal of the lens nucleus, removing the lens nucleus while the lens capsule is protected by the shield, and removing the shield after the removal of the lens nucleus by aspirating the gelatinous shield from the lens capsule.

4. A method of protecting a posterior lens capsule during removal of a lens nucleus, including the following steps, providing a flexible, deformable shield having an outer configuration of a size and shape to fit within the lens capsule at a position between the nucleus and the posterior capsule and to cover a substantial portion of the posterior capsule, providing an insertion tool, deforming the shield and positioning the deform shield with the insertion tool, inserting the insertion tool within the lens capsule, and providing the insertion-of the shield into the lens capsule by releasing the shield from the insertion tool and into the lens capsule into a position between the nucleus and the posterior capsule to protect the substantial portion of the posterior capsule during removal of the lens nucleus.

5. The method of claim 4 including the step of removing the lens nucleus and wherein the insertion tool is also used to provide an additional step of removing the shield from the lens capsule after the removal of the lens nucleus.

6. The method of claim 4 where the insertion tool is a cylindrical device, the shield is initially located within the cylindrical device and, after inserting the cylindrical device in the capsule the shield is ejected from the device into the desired position in the capsule.

7. A method of protecting a posterior lens capsule during removal of a lens nucleus, including the following steps, providing a flexible, deformable shield having an outer configuration of a size and shape to fit within the lens capsule at a position between the nucleus and the posterior capsule and to cover a substantial portion of the posterior capsule, inserting the shield into the lens capsule and into a position between the nucleus and the posterior capsule to protect the substantial portion of the posterior capsule during removal of the lens nucleus, and removing he lens nucleus, providing an intraocular lens and inserting the intraocular lens into the lens capsule while the shield maintains the lens capsule in an open position.

8. The method of claim 7 including the additional step of removing the shield from the lens capsule to allow the posterior capsule to collapse around the intraocular lens.

9. A method of protecting a posterior lens capsule during removal of a lens nucleus, including the following steps, providing a flexible, deformable shield having an outer configuration of a size and shape to fit within the lens capsule at a position between the nucleus and the posterior capsule and to cover a substantial portion of the posterior capsule, inserting the shield into the lens capsule and into a position between the nucleus and the posterior capsule to protect the substantial portion of the posterior capsule to protect the substantial portion of the posterior capsule during later removal of the lens nucleus, and wherein the shield is provided with a central area with dioptric power to from a combined shield/intraocular lens and with the additional step of removing the lens nucleus.

10. A method of protecting a posterior lens capsule during removal of a lens nucleus, including the following steps, providing a flexible, deformable shield having an outer configuration of a size and shape to fit within the lens capsule at a position between the nucleus and the posterior capsule and to cover a substantial portion of the posterior capsule, inserting the shield into the lens capsule and into a position between the nucleus and the posterior capsule to protect the substantial portion of the posterior capsule during later removal of the lens nucleus, and wherein the shield is provided with a roughened posterior surface and including the additional step of brushing the shield against the posterior capsule to remove epithelial and fibroblastic cells.

11. A method protecting a posterior lens capsule during removal of a lens nucleus, including the following the steps, providing a flexible, deformable shield having an anterior extension and an outer configuration of a size and shape to fit within the lens capsule at a position between the nucleus and the posterior capsule and to cover a substantial portion of the posterior capsule, inserting the shield into the lens capsule and into position between the nucleus and the posterior capsule during later removal of the lens nucleus, draping the anterior extension over the lens nucleus to protect the corneal endothelium, and wherein the shield including the anterior extension of the shield forms a basket containing the capsule nucleus and including the additional step of removing the shield plus anterior extension at the same time thereby also removing the capsule nucleus contained in the basket.

12. A method of cataract surgery including the following steps;

making a scleral or corneal incision in the eye to gain entrance into the eye, removing a portion of the anterior wall of the lens capsule, aspirating a substantial portion of the softer cortex material surrounding the dense nucleus within the lens capsule, providing a flexible shield having a size and shape to fit within the lens capsule, inserting the shield into the lens capsule in a position between the dense nucleus and the posterior capsule to protect the posterior capsule, and removing the dense nucleus from the lens capsule, and wherein the width of the incision is made to be less than the width of the shield after insertion.

13. The method of claim 12 wherein the shield is deformed prior to insertion through the incision into the lens capsule.

14. A method of cataract surgery including the following steps:

making a scleral or corneal incision in the eye to gain entrance into the eye, removing a portion of the anterior wall of the lens capsule, aspirating a substantial portion of the softer cortex material surrounding the dense nucleus within the lens capsule, providing a flexible shield having a size and shape to fit within the lens capsule, inserting the shield into the lens capsule in a position between the dense nucleus and the posterior capsule to protect the substantial portion of the posterior capsule, removing the dense nucleus from the lens capsule, and wherein the shield is provided with a C-shape cross section of material having an elastic memory and including the step of flattening the shield prior to insertion and allowing the shield to return to the C-shape configuration during and after insertion to follow the curvature of the dense nucleus and not push against the posterior capsule.

15. A method of cataract surgery including the following steps:

making a scleral or corneal incision in the eye to gain entrance into the eye, removing a portion of the anterior wall of the lens capsule, aspiration a substantial portion of the softer cortex material surrounding the dense nucleus within the lens capsule, providing a flexible shield with at least one opening having a size and shape to fit within the lens capsule and cover a substantial portion of the posterior capsule, inserting the shield into the lens capsule in a position between the dense nucleus and the posterior capsule to protect the substantial portion of the posterior capsule, and removing the dense nucleus from the lens capsule, providing an instrument with a hook-like end, inserting the instrument into the lens capsule to have the hook-like end of the instrument engage the opening in the shield, and removing the instrument and shield from the lens capsule by withdrawing the instrument.

16. A method of cataract surgery including the following steps;

making a scleral or corneal incision in the eye to gain entrance into the eye, removing a portion of the anterior wall of the lens capsule, aspirating a substantial portion of the softer cortex material surrounding the dense nucleus within the lens capsule, providing a flexible shield of gelatinous material having a size and shape to fit within the lens capsule, inserting the shield into the lens capsule in a position between the dense nucleus from the lens capsule to protect the posterior capsule, and removing the dense nucleus from the lens capsule, and removing the shield after the removal of the dense nucleus by aspirating the gelatinous shield from the lens capsule.

17. A method of cataract surgery including the following steps:

making a scleral or corneal incision in the eye to gain entrance into the eye, removing a portion of the anterior wall of the lens capsule, aspirating a substantial portion of the softer cortex material surrounding the dense nucleus within the lens capsule, providing a flexible shield having a size and shape to fit within the lens capsule, providing a cylindric insertion tool, deforming the shield and positioning the deformed shield within the insertion tool, inserting the insertion tool within the lens capsule, and providing the insertion of the shield into the lens capsule by forcing the shield out of the insertion tool and into the lens capsule in a position between the dense nucleus and the posterior capsule to protect the posterior capsule, and, removing the dense nucleus from the lens capsule.

18. The method of claim 17 wherein the insertion tool is also used to provide an additional step of removing the shield from the lens capsule after the removal of the dense nucleus.

19. A method of cataract surgery including the following steps:

making a scleral or corneal incision in the eye to gain entrance into the eye, removing a portion of the anterior wall of the lens capsule, aspirating a substantial portion of the softer cortex material surrounding the dense nucleus within the lens capsule, providing a flexible shield having a size and shape to fit within the lens capsule, inserting the shield into the lens capsule in a position between the dense nucleus and the posterior capsule to protect the posterior capsule, and removing the dense nucleus from the lens capsule, and providing an intraocular lens and inserting the intraocular lens into the lens capsule while the shield maintains the lens capsule in an open position.

20. The method of claim 19 including the additional step of removing the shield from the lens capsule to allow the posterior capsule to collapse around the intraocular lens.

21. A method of cataract surgery including the following steps:

making a scleral or corneal incision in the eye to gain entrance into the eye, removing a portion of the anterior wall of the lens capsule, aspirating a substantial portion of the softer cortex material surrounding the dense nucleus within the lens capsule, providing a flexible shield having a size and shape to fit within the lens capsule, inserting the shield into the lens capsule in a position between the dense nucleus and the posterior capsule to protect the posterior capsule, removing the dense nucleus from the lens capsule, and wherein the shield is provided with a central area with dioptric power to form a combined shield/intraocular lens.

22. A method of cataract surgery including the following steps:

making a scleral or corneal incision in the eye to gain entrance into the eye, removing a portion of the anterior wall of the lens capsule, aspirating a substantial portion of the softer cortex material surrounding the dense nucleus within the lens capsule, providing a flexible shield with a roughened posterior surface and having a size and shape to fit within the lens capsule, inserting the shield into the lens capsule in a position between the dense nucleus and the posterior capsule to protect the posterior capsule, removing the dense nucleus from the lens capsule, and brushing the shield against the posterior capsule to remove epithelial and fibroblastic cells.

23. A method of cataract surgery including the following steps:

making a scleral or corneal incision in the eye to gain entrance into the eye, removing a portion of the anterior wall of the lens capsule, aspirating a substantial portion of the softer cortex material surrounding the dense nucleus within the lens capsule, providing a flexible shield having a size and shape to fit within the lens capsule and having an anterior extension, inserting the shield into the lens capsule in a position between the dense nucleus and the posterior capsule to protect the posterior capsule, wherein the anterior extension is draped over the dense nucleus to protect the corneal endothelium, and wherein the shield plus the anterior extension form a basket containing the dense nucleus and including the additional step of removing the shield plus anterior extension at the same time thereby also removing the dense nucleus contained in the basket.

24. A method of protecting a posterior lens capsule during removal of a lens nucleus, including the following steps, providing a flexible, deformable shield having an outer configuration of a size and shape to fit within the lens capsule at a position between the nucleus and the posterior capsule and to cover a substantial portion of the posterior capsule, inserting the shield into the lens capsule and into a position between the nucleus and the posterior capsule to protect the posterior capsule during later removal of the lens nucleus, and wherein the shield is provided with a C-shape cross section of material having an elastic memory and including the step of flattening the shield prior to insertion and allowing the shield to return to the C-shape configuration during and after insertion to follow the curvature of the nucleus and not push against the posterior capsule.

25. A method of protecting a posterior lens capsule during removal of a lens nucleus, including the following steps, providing a viscous material to form when hardened, a flexible, deformable shield having an outer configuration of a size and shape to fit within the lens capsule at a position between the nucleus and the posterior capsule and to cover a substantial portion of the posterior capsule, injecting the viscous material into the lens capsule and into a position between the nucleus and the posterior capsule to protect the posterior capsule during later removal of the lens nucleus, and having the viscous material harden into a more solid state after injection.

26. A method of protecting a posterior lens capsule during removal of a lens nucleus, including the following steps, providing a flexible, deformable shield having an outer configuration of a size and shape to fit within the lens capsule at a position between the nucleus and the posterior capsule and to cover a substantial portion of the posterior capsule, inserting the shield into the lens capsule and into a position between the nucleus and the posterior capsule to protect the posterior capsule during removal of the lens nucleus, removing the lens nucleus while the lens capsule is protected by the shield, and wherein the shield is formed of a gelatinous material and including the additional step of removing the shield after the removal of the lens nucleus by aspirating the gelatinous shield from the lens capsule.

27. A method of protecting a posterior lens capsule during removal of a lens nucleus, including the following steps, providing a flexible, deformable shield having an outer configuration of a size and shape to fit within the lens capsule at a position between the nucleus and the posterior capsule and to cover a substantial portion of the posterior capsule, providing a cylindrical insertion tool, deforming the shield and positioning the deformed shield within the insertion tool, and inserting the insertion tool within the lens capsule and providing the insertion of the shield into the lens capsule by forcing the shield out of the insertion tool and into the lens capsule into a position between the nucleus and the posterior capsule to protect the posterior capsule during later removal of the lens nucleus.

28. The method of claim 27 wherein the insertion tool is also used to provide an additional step of removing the shield from the lens capsule after the removal of the lens nucleus.

29. A method of protecting a posterior lens capsule during removal of a lens nucleus, including the following steps, providing a flexible, deformable shield having an outer configuration of a size and shape to fit within the lens capsule at position beteen the nucleus and the posterior capsule and to cover a substantial portion of the posterior capsule, inserting the shield into the lens capsule and into a postion between the nucleus and the posterior capsule to protect the posterior capsule during later removal of the lens nucleus, and removing the lens nucleus, providing an intraocular lens and inserting the intraocular lens into the lens capsule while the shield maintains the lens capsule in an open position.

30. The method of claim 29 including the additional step of removing the shield from the lens capsule to allow the posterior capsule to collapse around the intraocular lens.

31. A method of protecting a posterior lens capsule during removal of a lens nucleus, including the following steps, providing a flexible, deformable shield having an outer configuration of a size and shape to fit within the lens capsule at a position between the nucleus and the posterior capsule and to cover a substantial portion of the posterior capsule, inserting the shield into the lens capsule and into a position between the nucleus and the posterior capsule to protect the posterior capsule during later removal of the lens nucleus, and wherein the shield is provided with a central area with dioptric power to form a combined shield/intraocular lens and with the additional step of removing the lens nucleus.

32. A method of protecting a posterior lens capsule during removal of a lens nucleus, including the following steps, providing a flexible, deformable shield having an outer configuration of a size and shape to fit within the lens capsule at a position between the nucleus and the posterior capsule and to cover a substantial portion of the posterior capsule, inserting the shield into the lens capsule and into a position between the nucleus and the posterior capsule to protect the posterior capsule during the later removal of the lens nucleus, and wherein the shield is provided with a roughened posterior surface and including the additional step of brushing the shield against the posterior capsule to remove epithelial and fibroblastic cells.

33. A method of protecting a posterior lens capsule during removal of a lens nucleus, including the following steps, providing a flexible, deformable shield having an outer configuration of a size and shape to fit within the lens capsule at a position between the nucleus and the posterior capsule and to cover a substantial portion of the posterior capsule, inserting the shield into the lens capsule and into a position between the nucleus and the posterior capsule to protect the posterior capsule during the later removal or the lens nucleus, wherein the shield is provided with an anterior extension and including the additional step of draping the anterior extension over the lens nucleus to protect the corneal endothelium, and wherein the shield including the anterior extension of the shield forms a basket containing the capsule nucleus and including the additional step or removing the shield plus anterior extension at the same time thereby also removing the capsule nucleus contained in the basket.

* * * * *